US012773159B2

(12) United States Patent
Arnholt et al.

(10) Patent No.: US 12,773,159 B2
(45) Date of Patent: Oct. 27, 2026

(54) INTERACTIVE MEDICAL VISUALIZATION SYSTEM AND METHODS FOR VISUALIZING STIMULATION LEAD PLACEMENT

(71) Applicant: Cardiac Pacemakers, Inc., St. Paul, MN (US)

(72) Inventors: Devon N. Arnholt, Shoreview, MN (US); Michael J. Kane, St. Paul, MN (US); Brian L. Schmidt, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 370 days.

(21) Appl. No.: 18/214,065

(22) Filed: Jun. 26, 2023

(65) Prior Publication Data

US 2023/0414161 A1 Dec. 28, 2023

Related U.S. Application Data

(60) Provisional application No. 63/355,728, filed on Jun. 27, 2022.

(51) Int. Cl.

| | |
|---|---|
| ***A61B 5/00*** | (2006.01) |
| ***A61N 1/36*** | (2006.01) |
| *A61B 5/055* | (2006.01) |

(52) U.S. Cl.

CPC .......... *A61B 5/4064* (2013.01); *A61B 5/0022* (2013.01); *A61N 1/3606* (2013.01); *A61B 5/055* (2013.01)

(58) Field of Classification Search

CPC ..... A61B 5/4064; A61B 5/0022; A61B 5/055; A61B 34/25; A61B 2034/104;

(Continued)

(56) References Cited

U.S. PATENT DOCUMENTS 6,273,896 B1 * 8/2001 Franck .................. A61B 90/10 606/130
9,020,789 B2 4/2015 Butson et al.

(Continued)

OTHER PUBLICATIONS

"Invitation to Pay Additional Fees," for PCT Application No. PCT/US2023/026222 mailed Oct. 6, 2023 (8 pages).

(Continued)

*Primary Examiner* — Scott M. Getzow

(57) ABSTRACT

Embodiments herein relate to interactive medical visualization systems for visualizing stimulation lead placements and related methods. In an embodiment, a medical visualization system can be included having a video processing circuit, a central processing circuit in communication with the video processing circuit, and a user interface. The user interface can be generated by the video processing circuit and can include a three-dimensional model. The three-dimensional model can include at least a portion of a subject's anatomy and a graphic representation including at least one cancer therapy stimulation lead, and a visual thermal heating zone associated with the graphic representation of the at least one cancer therapy stimulation lead and/or a visual electrical field strength zone associated with the graphic representation of the at least one cancer therapy stimulation lead. Other embodiments are also included herein.

20 Claims, 15 Drawing Sheets

(58) Field of Classification Search
CPC ............ A61B 2034/105; A61B 18/148; A61B 2018/00446; A61B 2018/00982; A61B 34/10; A61B 2034/107; A61N 1/3606; A61N 1/0539; A61N 1/0534; A61N 1/36002
See application file for complete search history.

(56) References Cited

U.S. PATENT DOCUMENTS

| | | | | |
|---|---|---|---|---|
| 9,307,925 | B2 | 4/2016 | Russell et al. | |
| 10,188,851 | B2 | 1/2019 | Wenger et al. | |
| 11,013,909 | B2 | 5/2021 | Wenger et al. | |
| 2010/0312094 | A1* | 12/2010 | Guttman ................ | A61B 34/20 600/411 |
| 2015/0320481 | A1* | 11/2015 | Cosman, Jr. ....... | A61B 18/1233 606/35 |
| 2016/0081577 | A1 | 3/2016 | Sridhar et al. | |
| 2019/0117956 | A1 | 4/2019 | Wenger et al. | |
| 2019/0117972 | A1 | 4/2019 | Schmidt et al. | |
| 2021/0369394 | A1 | 12/2021 | Braido et al. | |
| 2023/0218894 | A1 | 7/2023 | Arnholt et al. | |
| 2023/0329748 | A1* | 10/2023 | Sowards ................ | A61B 8/488 |

OTHER PUBLICATIONS

"International Search Report and Written Opinion," for PCT Application No. PCT/US2023/026222 mailed Nov. 27, 2023 (15 pages).

* cited by examiner

INTERACTIVE MEDICAL VISUALIZATION SYSTEM AND METHODS FOR VISUALIZING STIMULATION LEAD PLACEMENT

This application claims the benefit of U.S. Provisional Application No. 63/355,728, filed Jun. 27, 2022, the content of which is herein incorporated by reference in its entirety.

FIELD

Embodiments herein relate to interactive medical visualization systems for visualizing stimulation lead placements and related methods.

BACKGROUND

Various forms of brain cancer such as glioblastoma, meningioma, and the like can be treated using electrical stimulation. However, the correct placement of the electrodes is important to be able to effectively treat the conditions and prevent damage to the subject's non-targeted brain tissue, blood vessels, and nerves.

Many instruments with optics or electronic imaging cameras allow for the visual observation of a subject's internal organs that would otherwise be difficult to see. For example, bronchoscopes, endoscopes, and the like have all allowed clinicians to visually observe portions of a subject's anatomy that are otherwise hidden.

Similarly, many techniques for medical imaging also allow clinicians to visually observe portions of a subject's anatomy. These techniques can include X-ray radiography, fluoroscopy, computerized axial tomography (CAT), and magnetic resonance imaging (Mill). However, many of these techniques are two-dimensional or render two-dimensional displays which can make the results difficult to interpret or challenging to apply the results in a subsequent procedure.

SUMMARY

Embodiments herein relate to interactive medical visualization systems for visualizing stimulation lead placements and related methods. In a first aspect, a medical visualization system can be included having a video processing circuit, a central processing circuit in communication with the video processing circuit, and a user interface. The user interface can be generated by the video processing circuit and can include a three-dimensional model. The three-dimensional model can include at least a portion of a subject's anatomy and a graphic representation including at least one cancer therapy stimulation lead, and a visual thermal heating zone associated with the graphic representation of the at least one cancer therapy stimulation lead.

In a second aspect, in addition to one or more of the preceding or following aspects, or in the alternative to some aspects, the visual thermal heating zone provides a graphic representation of temperatures around the at least one cancer therapy stimulation lead.

In a third aspect, in addition to one or more of the preceding or following aspects, or in the alternative to some aspects, the visual thermal heating zone provides a graphic representation of temperatures around tissue adjacent to the at least one cancer therapy stimulation lead.

In a fourth aspect, in addition to one or more of the preceding or following aspects, or in the alternative to some aspects, the three-dimensional model further can include at least one selected from the group consisting of patient data gathered in real-time, previously stored patient data, and idealized model data.

In a fifth aspect, in addition to one or more of the preceding or following aspects, or in the alternative to some aspects, the video processing circuit can be remotely located from a machine displaying the user interface.

In a sixth aspect, in addition to one or more of the preceding or following aspects, or in the alternative to some aspects, the video processing circuit can be co-located with a machine displaying the user interface.

In a seventh aspect, in addition to one or more of the preceding or following aspects, or in the alternative to some aspects, the three-dimensional model further can include a cancerous tumor, resection cavity, and/or a contrast enhanced region.

In an eighth aspect, in addition to one or more of the preceding or following aspects, or in the alternative to some aspects, the graphic representation of the at least one cancer therapy stimulation lead can be shown to be positioned at or near a site of the cancerous tumor, resection cavity, and/or the contrast enhanced region.

In a ninth aspect, in addition to one or more of the preceding or following aspects, or in the alternative to some aspects, the graphic representation of the at least one cancer therapy stimulation lead can be shown to be positioned within the cancerous tumor, resection cavity, and/or the contrast enhanced region.

In a tenth aspect, in addition to one or more of the preceding or following aspects, or in the alternative to some aspects, the graphic representation further can include three cancer therapy stimulation leads, wherein the three cancer therapy stimulation leads can be shown to be positioned about a center point of the cancerous tumor, resection cavity, and/or the contrast enhanced region.

In an eleventh aspect, in addition to one or more of the preceding or following aspects, or in the alternative to some aspects, the three cancer therapy stimulation leads can be shown to be positioned about 120 degrees about the center point of the cancerous tumor, resection cavity, and/or the contrast enhanced region.

In a twelfth aspect, in addition to one or more of the preceding or following aspects, or in the alternative to some aspects, the graphic representation further can include four cancer therapy stimulation leads, wherein the four cancer therapy stimulation leads can be shown to be positioned about a center point the cancerous tumor, resection cavity, and/or the contrast enhanced region.

In a thirteenth aspect, in addition to one or more of the preceding or following aspects, or in the alternative to some aspects, the graphic representation of the four cancer therapy stimulation leads can be shown to be positioned about 90 degrees about the center point of the cancerous tumor, resection cavity, and/or the contrast enhanced region.

In a fourteenth aspect, in addition to one or more of the preceding or following aspects, or in the alternative to some aspects, the user interface displays an electrode position to provide a therapy based on a location of the cancerous tumor, resection cavity, and/or the contrast enhanced region.

In a fifteenth aspect, in addition to one or more of the preceding or following aspects, or in the alternative to some aspects, the user interface displays placement of one or more cancer therapy stimulation leads based on a location the cancerous tumor, resection cavity, and/or the contrast enhanced region.

In a sixteenth aspect, in addition to one or more of the preceding or following aspects, or in the alternative to some aspects, the user interface displays placement of one or more electrodes based on a location of the cancerous tumor, resection cavity, and/or the contrast enhanced region.

In a seventeenth aspect, in addition to one or more of the preceding or following aspects, or in the alternative to some aspects, the user interface displays a predetermined therapy parameter can include a duty cycle based on a location the cancerous tumor, resection cavity, and/or the contrast enhanced region.

In an eighteenth aspect, in addition to one or more of the preceding or following aspects, or in the alternative to some aspects, the at least one cancer therapy stimulation lead can include at least one electrode.

In a nineteenth aspect, in addition to one or more of the preceding or following aspects, or in the alternative to some aspects, the at least one electrode can be insulated to induce directionality of a field strength.

In a twentieth aspect, in addition to one or more of the preceding or following aspects, or in the alternative to some aspects, the at least one electrode can include a heat shield, wherein the heat shield can be configured to shape an electric field of the at least one electrode.

In a twenty-first aspect, in addition to one or more of the preceding or following aspects, or in the alternative to some aspects, the at least one cancer therapy stimulation lead can include two electrodes.

In a twenty-second aspect, in addition to one or more of the preceding or following aspects, or in the alternative to some aspects, the at least a portion of a subject's anatomy can include at least one selected from the group consisting of brain, heart, pancreas, lungs, liver, uterus, ovaries, stomach, prostate gland, kidney, thyroid, bladder, and intestines.

In a twenty-third aspect, in addition to one or more of the preceding or following aspects, or in the alternative to some aspects, wherein the three-dimensional model can be configured to present placement of the at least one cancer therapy stimulation lead, and wherein the at least one cancer therapy stimulation lead can be placed to avoid one or more critical structures.

In a twenty-fourth aspect, in addition to one or more of the preceding or following aspects, or in the alternative to some aspects, the user interface notifies the user of a field strength.

In a twenty-fifth aspect, in addition to one or more of the preceding or following aspects, or in the alternative to some aspects, the user interface notifies the user of placing one or more additional cancer therapy stimulation leads to increase a field strength.

In a twenty-sixth aspect, in addition to one or more of the preceding or following aspects, or in the alternative to some aspects, the user interface notifies the user when the at least one cancer therapy stimulation lead can be near a critical structure.

In a twenty-seventh aspect, in addition to one or more of the preceding or following aspects, or in the alternative to some aspects, the critical structure can include at least one selected from the group consisting of bone, pituitary gland, blood vessels, hypothalamus, brain ventricles, brain stem, amygdala, thalamus, cerebellum, and corpus callosum.

In a twenty-eighth aspect, in addition to one or more of the preceding or following aspects, or in the alternative to some aspects, the user interface notifies the user when a calculated temperature of a critical structure or other designated area exceeds a programmable maximum temperature value.

In a twenty-ninth aspect, in addition to one or more of the preceding or following aspects, or in the alternative to some aspects, the user interface further can include at least one visual burr hole representation, wherein the at least one visual burr hole representation provides a graphic representation of optimal burr hole placement.

In a thirtieth aspect, in addition to one or more of the preceding or following aspects, or in the alternative to some aspects, the at least one visual burr hole representation can be shown to be at least ¼ inch in diameter.

In a thirty-first aspect, in addition to one or more of the preceding or following aspects, or in the alternative to some aspects, the at least one visual burr hole representation can be shown to be approximately ⅝ inches in diameter.

In a thirty-second aspect, in addition to one or more of the preceding or following aspects, or in the alternative to some aspects, the user interface further can include a visual lead trajectory, wherein the visual lead trajectory provides a graphic representation of an optimal trajectory of the at least one cancer therapy stimulation lead.

In a thirty-third aspect, in addition to one or more of the preceding or following aspects, or in the alternative to some aspects, the user interface further can include a visual thermal representation of the at least a portion of a subject's anatomy, wherein the visual thermal representation of the at least a portion of a subject's anatomy can be associated with the three-dimensional model.

In a thirty-fourth aspect, in addition to one or more of the preceding or following aspects, or in the alternative to some aspects, the visual thermal representation of the at least a portion of a subject's anatomy estimates temperatures throughout the three-dimensional model.

In a thirty-fifth aspect, in addition to one or more of the preceding or following aspects, or in the alternative to some aspects, wherein aspects of the visual thermal heating zone can be calculated based on a power for electrodes disposed on the at least one cancer therapy stimulation lead and a duty factor setting.

In a thirty-sixth aspect, in addition to one or more of the preceding or following aspects, or in the alternative to some aspects, the user interface can be configured to display one or more therapy vector patterns between electrodes.

In a thirty-seventh aspect, in addition to one or more of the preceding or following aspects, or in the alternative to some aspects, wherein aspects of the visual thermal heating zone can be calculated based on therapy vector patterns between electrodes, a power for the electrodes, and a duty factor for the electrodes.

In a thirty-eighth aspect, a medical visualization system can be included having a video processing circuit, a central processing circuit in communication with the video processing circuit, and a user interface, wherein the user interface can be generated by a video processing circuit. The user interface can include a three-dimensional model, the three-dimensional model can include at least a portion of a subject's anatomy, and a graphic representation including at least one cancer therapy stimulation lead, and a visual thermal heating zone. The visual thermal heating zone can be associated with a graphic representation of at least one cancer therapy stimulation lead. The system can also include a notification system, wherein the notification system can be configured to provide one or more notifications to the user.

In a thirty-ninth aspect, in addition to one or more of the preceding or following aspects, or in the alternative to some aspects, the notification system notifies the user when the at least one cancer therapy stimulation lead can be near one or more critical structures.

In a fortieth aspect, in addition to one or more of the preceding or following aspects, or in the alternative to some aspects, the critical structure can include at least one selected from the group consisting of bone, pituitary gland, blood vessels, hypothalamus, brain ventricles, brain stem, amygdala, thalamus, cerebellum, and corpus callosum.

In a forty-first aspect, in addition to one or more of the preceding or following aspects, or in the alternative to some aspects, the medical visualization system notifies the user when a calculated temperature of a critical structure or other designated area exceeds a programmable maximum temperature value.

In a forty-second aspect, in addition to one or more of the preceding or following aspects, or in the alternative to some aspects, the notification system notifies the user of placing one or more additional cancer therapy stimulation leads to increase a field strength.

In a forty-third aspect, in addition to one or more of the preceding or following aspects, or in the alternative to some aspects, the notification system notifies the user of placing one or more additional electrodes to increase a field strength.

In a forty-fourth aspect, in addition to one or more of the preceding or following aspects, or in the alternative to some aspects, the one or more additional electrodes can include at least one selected from the group consisting of subcutaneous electrode, subcranial electrode, and external electrode.

In a forty-fifth aspect, in addition to one or more of the preceding or following aspects, or in the alternative to some aspects, the notification system notifies the user of a field strength.

In a forty-sixth aspect, in addition to one or more of the preceding or following aspects, or in the alternative to some aspects, the notification system can include at least one selected from the group consisting of pop-up alert, sound alert, textural change in the graphic representation, and color change in the graphic representation.

In a forty-seventh aspect, a method for visualizing cancer treatment lead placement can be included, the method including obtaining three-dimensional imaging data of a region of tissue at or near a cancerous tumor, resection cavity, and/or the contrast enhanced region, generating a predetermined model to using the three-dimensional imaging data, wherein the predetermined model can be configured to assign one or more electrical properties to the region of tissue, positioning one or more cancer therapy stimulation leads into the region of tissue within the predetermined model at or near the cancerous tumor, resection cavity, and/or the contrast enhanced region, and calculating one or more electric fields to the region of tissue at or near the cancerous tumor, resection cavity, and/or the contrast enhanced region and superimposing one or more electric field lines on the predetermined model.

In a forty-eighth aspect, in addition to one or more of the preceding or following aspects, or in the alternative to some aspects, the method can further include calculating one or more temperatures of the region of tissue at or near the cancerous tumor, resection cavity, and/or the contrast enhanced region and superimposing one or more temperature contours onto the predetermined model.

In a forty-ninth aspect, in addition to one or more of the preceding or following aspects, or in the alternative to some aspects, where the predetermined model can be configured to predict changes to the region of tissue over a period of time.

In a fiftieth aspect, in addition to one or more of the preceding or following aspects, or in the alternative to some aspects, the changes result from a void or tissue swelling left behind by a resection of the cancerous tumor, resection cavity, and/or the contrast enhanced region.

In a fifty-first aspect, in addition to one or more of the preceding or following aspects, or in the alternative to some aspects, the one or more electrical properties can be assigned based on the type of tissue.

In a fifty-second aspect, in addition to one or more of the preceding or following aspects, or in the alternative to some aspects, the type of tissue can include at least one selected from the group consisting of cancerous tissue, muscle, bone, and healthy tissue.

In a fifty-third aspect, in addition to one or more of the preceding or following aspects, or in the alternative to some aspects, the method can further include setting a maximum temperature limit for healthy tissue.

In a fifty-fourth aspect, in addition to one or more of the preceding or following aspects, or in the alternative to some aspects, the method can further include notifying a system user when a calculated temperature of a critical structure or other designated area exceeds the maximum temperature limit.

In a fifty-fifth aspect, in addition to one or more of the preceding or following aspects, or in the alternative to some aspects, the method can further include setting a maximum temperature limit for cancerous tissue.

In a fifty-sixth aspect, in addition to one or more of the preceding or following aspects, or in the alternative to some aspects, the method can further include notifying a system user when a calculated temperature of a cancerous tissue exceeds the maximum temperature limit.

In a fifty-seventh aspect, in addition to one or more of the preceding or following aspects, or in the alternative to some aspects, the method can further include setting a minimum electric field strength.

In a fifty-eighth aspect, in addition to one or more of the preceding or following aspects, or in the alternative to some aspects, the one or more cancer therapy stimulation leads can be independently controlled.

In a fifty-ninth aspect, in addition to one or more of the preceding or following aspects, or in the alternative to some aspects, the one or more cancer therapy stimulation leads include one or more electrodes.

In a sixtieth aspect, in addition to one or more of the preceding or following aspects, or in the alternative to some aspects, wherein the one or more cancer therapy stimulation leads include a temperature measurement component.

In a sixty-first aspect, in addition to one or more of the preceding or following aspects, or in the alternative to some aspects, the one or more cancer therapy stimulation leads include a heat gradient and a therapy gradient extending outward from the one or more cancer therapy stimulation leads.

In a sixty-second aspect, in addition to one or more of the preceding or following aspects, or in the alternative to some aspects, the three-dimensional imaging data can be obtained using magnetic resonance imaging data or computerized tomography data.

In a sixty-third aspect, a medical visualization system can be included having a video processing circuit, a central processing circuit in communication with the video processing circuit, and a user interface, wherein the user interface can be generated by the video processing circuit. The user interface can include a three-dimensional model including at least a portion of a subject's anatomy and a graphic representation including at least one cancer therapy stimulation lead and a visual electrical field strength zone. The visual electrical field strength zone can be associated with the graphic representation of the at least one cancer therapy stimulation lead.

In a sixty-fourth aspect, in addition to one or more of the preceding or following aspects, or in the alternative to some aspects, the visual electrical field strength zone includes a graphic representation of electrical field strength around the at least one cancer therapy stimulation lead.

In a sixty-fifth aspect, in addition to one or more of the preceding or following aspects, or in the alternative to some aspects, the three-dimensional model further can include at least one selected from the group consisting of patient data gathered in real-time, previously stored patient data, and idealized model data.

In a sixty-sixth aspect, in addition to one or more of the preceding or following aspects, or in the alternative to some aspects, the three-dimensional model further can include a cancerous tumor, resection cavity, and/or a contrast enhanced region.

In a sixty-seventh aspect, in addition to one or more of the preceding or following aspects, or in the alternative to some aspects, the graphic representation of the at least one cancer therapy stimulation lead can be shown to be positioned at or near a site of the cancerous tumor, resection cavity, and/or the contrast enhanced region.

In a sixty-eighth aspect, in addition to one or more of the preceding or following aspects, or in the alternative to some aspects, the graphic representation of the at least one cancer therapy stimulation lead can be shown to be positioned within the cancerous tumor, resection cavity, and/or the contrast enhanced region.

In a sixty-ninth aspect, in addition to one or more of the preceding or following aspects, or in the alternative to some aspects, the user interface displays an electrode position to provide a therapy based on a location of the cancerous tumor, resection cavity, and/or the contrast enhanced region.

In a seventieth aspect, in addition to one or more of the preceding or following aspects, or in the alternative to some aspects, the user interface displays placement of one or more cancer therapy stimulation leads based on a location the cancerous tumor, resection cavity, and/or the contrast enhanced region.

In a seventy-first aspect, in addition to one or more of the preceding or following aspects, or in the alternative to some aspects, the user interface displays placement of one or more electrodes based on a location of the cancerous tumor, resection cavity, and/or the contrast enhanced region.

In a seventy-second aspect, in addition to one or more of the preceding or following aspects, or in the alternative to some aspects, the user interface displays a predetermined therapy parameter can include a duty cycle based on a location the cancerous tumor, resection cavity, and/or the contrast enhanced region.

In a seventy-third aspect, in addition to one or more of the preceding or following aspects, or in the alternative to some aspects, the at least a portion of a subject's anatomy can include at least one selected from the group consisting of brain, heart, pancreas, lungs, liver, uterus, ovaries, stomach, prostate gland, kidney, thyroid, bladder, and intestines.

In a seventy-fourth aspect, in addition to one or more of the preceding or following aspects, or in the alternative to some aspects, wherein the three-dimensional model can be configured to present placement of the at least one cancer therapy stimulation lead, and wherein the at least one cancer therapy stimulation lead can be positioned to avoid one or more critical structures.

In a seventy-fifth aspect, in addition to one or more of the preceding or following aspects, or in the alternative to some aspects, the user interface notifies the user of a field strength.

In a seventy-sixth aspect, in addition to one or more of the preceding or following aspects, or in the alternative to some aspects, the user interface notifies the user of placing one or more additional cancer therapy stimulation leads to increase a field strength.

In a seventy-seventh aspect, in addition to one or more of the preceding or following aspects, or in the alternative to some aspects, the user interface notifies the user when the at least one cancer therapy stimulation lead can be near a critical structure.

In a seventy-eighth aspect, in addition to one or more of the preceding or following aspects, or in the alternative to some aspects, the critical structure can include at least one selected from the group consisting of bone, pituitary gland, blood vessels, hypothalamus, brain ventricles, brain stem, amygdala, thalamus, cerebellum, and corpus callosum.

In a seventy-ninth aspect, in addition to one or more of the preceding or following aspects, or in the alternative to some aspects, the user interface further can include at least one visual burr hole representation, wherein the at least one visual burr hole representation provides a graphic representation of optimal burr hole placement.

In an eightieth aspect, in addition to one or more of the preceding or following aspects, or in the alternative to some aspects, the user interface further can include a visual lead trajectory, wherein the visual lead trajectory provides a graphic representation of an optimal trajectory of the at least one cancer therapy stimulation lead.

In an eighty-first aspect, in addition to one or more of the preceding or following aspects, or in the alternative to some aspects, the user interface further can include a visual thermal representation of the at least a portion of a subject's anatomy, wherein the visual thermal representation can be associated with the three-dimensional model.

In an eighty-second aspect, in addition to one or more of the preceding or following aspects, or in the alternative to some aspects, the visual thermal representation includes estimates of temperatures throughout the three-dimensional model.

In an eighty-third aspect, in addition to one or more of the preceding or following aspects, or in the alternative to some aspects, the user interface notifies the user when an estimated temperature of a critical structure or other designated area exceeds a programmable maximum temperature value.

In an eighty-fourth aspect, in addition to one or more of the preceding or following aspects, or in the alternative to some aspects, the user interface can be configured to display one or more therapy vector patterns between electrodes.

In an eighty-fifth aspect, a medical visualization system can be included having a video processing circuit, a central processing circuit, wherein the central processing circuit can be in communication with the video processing circuit, and a user interface, wherein the user interface can be generated by the video processing circuit, the user interface can include a three-dimensional model, the three-dimensional model can include at least a portion of a subject's anatomy, a graphic representation, the graphic representation can include at least one cancer therapy stimulation lead, a visual thermal heating zone, wherein the visual thermal heating zone can be associated with the graphic representation of the at least one cancer therapy stimulation lead, and a visual electrical field strength zone, wherein the visual electrical field strength zone can be associated with the graphic representation of the at least one cancer therapy stimulation lead.

In an eighty-sixth aspect, in addition to one or more of the preceding or following aspects, or in the alternative to some aspects, the visual thermal heating zone includes a graphic representation of temperatures around the at least one cancer therapy stimulation lead.

In an eighty-seventh aspect, in addition to one or more of the preceding or following aspects, or in the alternative to some aspects, the visual thermal heating zone includes a graphic representation of temperatures around tissue adjacent to the at least one cancer therapy stimulation lead.

In an eighty-eighth aspect, in addition to one or more of the preceding or following aspects, or in the alternative to some aspects, the visual electrical field strength zone includes a graphic representation of electrical field strength around the at least one cancer therapy stimulation lead.

In an eighty-ninth aspect, in addition to one or more of the preceding or following aspects, or in the alternative to some aspects, the visual electrical field strength zone includes a graphic representation of electrical field strength around tissue adjacent to the at least one cancer therapy stimulation lead.

In a ninetieth aspect, in addition to one or more of the preceding or following aspects, or in the alternative to some aspects, wherein one of the visual thermal heating zone and the visual electrical field strength zone can be superimposed over the other.

In a ninety-first aspect, in addition to one or more of the preceding or following aspects, or in the alternative to some aspects, the three-dimensional model further can include at least one selected from the group consisting of patient data gathered in real-time, previously stored patient data, and idealized model data.

In a ninety-second aspect, in addition to one or more of the preceding or following aspects, or in the alternative to some aspects, the three-dimensional model further can include a cancerous tumor, resection cavity, and/or the contrast enhanced region.

In a ninety-third aspect, in addition to one or more of the preceding or following aspects, or in the alternative to some aspects, the graphic representation of the at least one cancer therapy stimulation lead can be shown to be positioned at or near a site of the cancerous tumor, resection cavity, and/or the contrast enhanced region.

In a ninety-fourth aspect, in addition to one or more of the preceding or following aspects, or in the alternative to some aspects, the graphic representation of the at least one cancer therapy stimulation lead can be shown to be positioned within the cancerous tumor, resection cavity, and/or the contrast enhanced region.

In a ninety-fifth aspect, in addition to one or more of the preceding or following aspects, or in the alternative to some aspects, the user interface displays an electrode position to provide a therapy based on a location of the cancerous tumor, resection cavity, and/or the contrast enhanced region.

In a ninety-sixth aspect, in addition to one or more of the preceding or following aspects, or in the alternative to some aspects, the user interface displays placement of one or more cancer therapy stimulation leads based on a location the cancerous tumor, resection cavity, and/or the contrast enhanced region.

In a ninety-seventh aspect, in addition to one or more of the preceding or following aspects, or in the alternative to some aspects, the user interface displays placement of one or more electrodes based on a location of the cancerous tumor, resection cavity, and/or the contrast enhanced region.

In a ninety-eighth aspect, in addition to one or more of the preceding or following aspects, or in the alternative to some aspects, the user interface displays a predetermined therapy parameter can include a duty cycle based on a location the cancerous tumor, resection cavity, and/or the contrast enhanced region.

In a ninety-ninth aspect, in addition to one or more of the preceding or following aspects, or in the alternative to some aspects, the at least a portion of a subject's anatomy can include at least one selected from the group consisting of brain, heart, pancreas, lungs, liver, uterus, ovaries, stomach, prostate gland, kidney, thyroid, bladder, and intestines.

In a one hundredth aspect, in addition to one or more of the preceding or following aspects, or in the alternative to some aspects, the three-dimensional model can be configured to present placement of the at least one cancer therapy stimulation lead, and wherein the at least one cancer therapy stimulation lead can be positioned to avoid one or more critical structures.

In a one hundred and first aspect, in addition to one or more of the preceding or following aspects, or in the alternative to some aspects, the user interface notifies the user of a field strength.

In a one hundred and second aspect, in addition to one or more of the preceding or following aspects, or in the alternative to some aspects, the user interface notifies the user of placing one or more additional cancer therapy stimulation leads to increase a field strength.

In a one hundred and third aspect, in addition to one or more of the preceding or following aspects, or in the alternative to some aspects, the user interface notifies the user when the at least one cancer therapy stimulation lead can be near a critical structure.

In a one hundred and fourth aspect, in addition to one or more of the preceding or following aspects, or in the alternative to some aspects, the critical structure can include at least one selected from the group consisting of bone, pituitary gland, blood vessels, hypothalamus, brain ventricles, brain stem, amygdala, thalamus, cerebellum, and corpus callosum.

In a one hundred and fifth aspect, in addition to one or more of the preceding or following aspects, or in the alternative to some aspects, the user interface further can include at least one visual burr hole representation, wherein the at least one visual burr hole representation provides a graphic representation of optimal burr hole placement.

In a one hundred and sixth aspect, in addition to one or more of the preceding or following aspects, or in the alternative to some aspects, the user interface further can include a visual lead trajectory, wherein the visual lead trajectory provides a graphic representation of an optimal trajectory of the at least one cancer therapy stimulation lead.

In a one hundred and seventh aspect, in addition to one or more of the preceding or following aspects, or in the alternative to some aspects, the user interface further can include a visual thermal representation of the at least a portion of a subject's anatomy, wherein the visual thermal representation of the at least a portion of a subject's anatomy can be associated with the three-dimensional model.

In a one hundred and eighth aspect, in addition to one or more of the preceding or following aspects, or in the alternative to some aspects, the visual thermal representation of the at least a portion of a subject's anatomy estimates temperatures throughout the three-dimensional model.

In a one hundred and ninth aspect, in addition to one or more of the preceding or following aspects, or in the alternative to some aspects, wherein aspects of the visual thermal representation of the at least a portion of a subject's anatomy can be calculated based on a power for electrodes disposed on the at least one cancer therapy stimulation lead and a duty factor setting.

In a one hundred and tenth aspect, in addition to one or more of the preceding or following aspects, or in the alternative to some aspects, wherein aspects of the visual thermal representation of the at least a portion of a subject's anatomy can be calculated based on therapy vector patterns between electrodes, a power for the electrodes, and a duty factor for the electrodes.

In a one hundred and eleventh aspect, in addition to one or more of the preceding or following aspects, or in the alternative to some aspects, the user interface can be configured to display one or more therapy vector patterns between electrodes.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Many techniques for medical imaging allow clinicians to observe portions of a subject's anatomy and gather anatomical data. These techniques can include X-ray radiography, fluoroscopy, computerized axial tomography (CAT), ultrasound and magnetic resonance imaging (MRI). However, many of these techniques render displays that are difficult to interpret or are otherwise challenging to apply to a subsequent procedure.

Many invasive procedures can require the correct placement of medical device equipment, such as electrical stimulation leads. The correct placement of various devices in certain areas of a subject's anatomy is critical to providing targeted therapies. In some scenarios the correct placement of devices is also critical to minimizing damage to surrounding healthy tissues. For example, when placing electrical stimulation leads that apply an electric field strength sufficient to provide therapy when treating a tumor resection site or cavity or a tumor itself, it is important cause as little damage as possible to surrounding healthy tissue, including blood vessels, or nerves. The need to minimize damage to healthy tissue is particularly great in the context of tumor resection sites or tumors in the head.

Embodiments herein relate to an interactive medical visualization system for determining the placement of electrical stimulation leads using a three-dimensional model of a subject's anatomy and virtual stimulation leads. The medical visualization system can use the three-dimensional model of a subject's anatomy to inform optimized placement of electrical stimulation leads in a subject's anatomy and can also provide interactive capabilities for a user to refine planned placement of the electrical stimulation leads prior to a surgical procedure for actual placement. As discussed herein, the visual placement of the electrical stimulation leads can be optimized for treatment of the subject's anatomy and safety of the subject. In addition, the medical visualization system can be configured to provide a user with interactive capabilities to identify how different possible placements of the virtual stimulation leads can focus a therapy on a desired target area while sparing tissue damage to healthy tissues.

Figure 1:
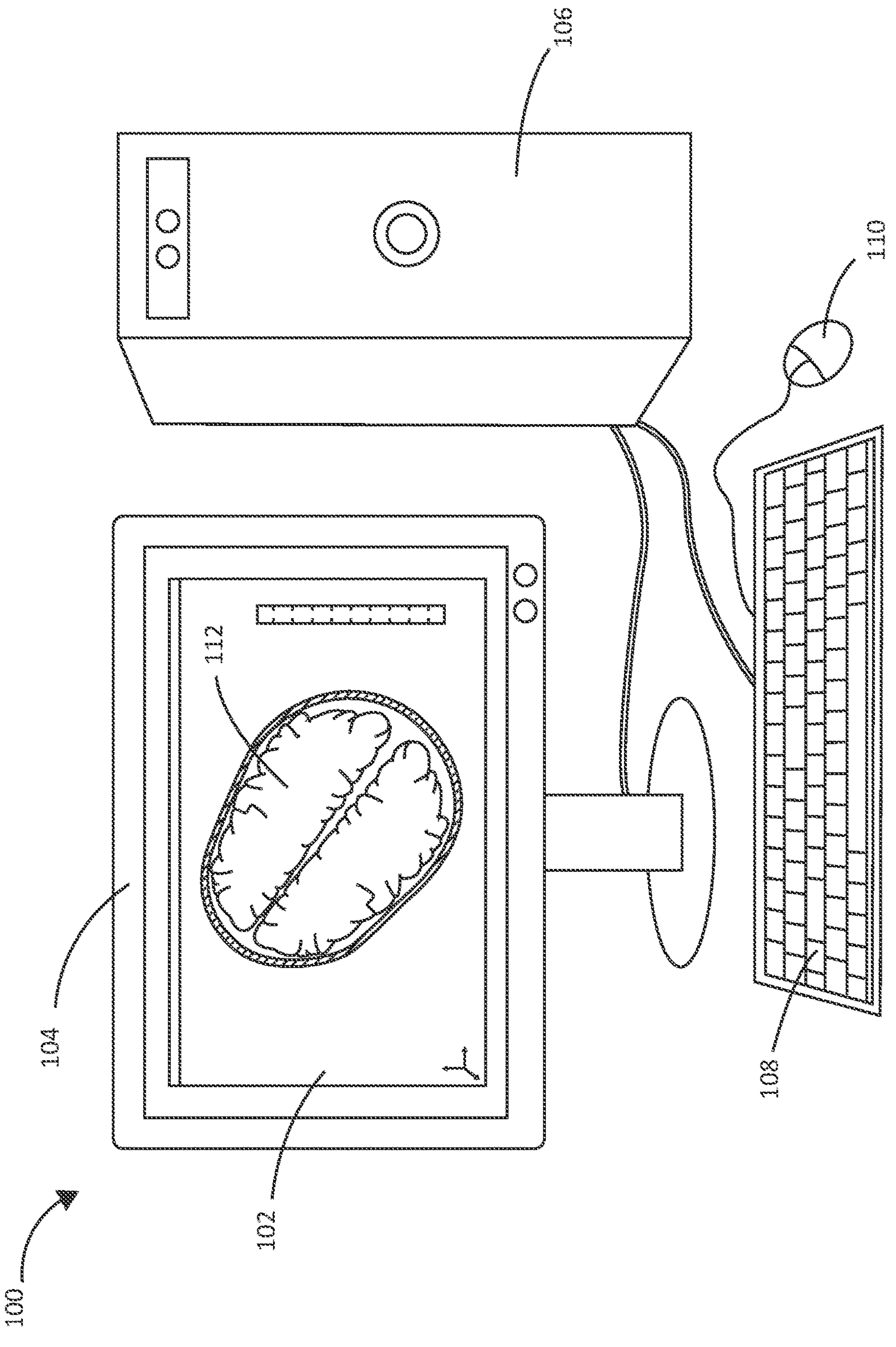
FIG. 1 is a schematic view of a medical visualization system in accordance with various embodiments herein.

Referring now to FIG. 1, a schematic view of a medical visualization system 100 is shown in accordance with various embodiments herein. The medical visualization system 100 can include a user interface 102. The user interface 102 can be generated by a video processing circuit (discussed in greater detail below) and projected to the user on a video display 104. The video processing circuit can be local to a user's computer 106 or it can be located at a central node or server, on or off site. In various embodiments, the video processing circuit is co-located with a computer displaying the user interface. The medical visualization system 100 can be configured to accept input from a user via various user interface devices, including, but not to be limited to, a keyboard 108 and/or a computer mouse 110. It will be appreciated that various additional user interface devices can be contemplated herein, including one or more of a keyboard, a mouse, a joystick, a touchpad, a touch screen, a smart pen, a stylus, voice commands, and the like.

The user interface 102 of medical visualization system 100 can include various features presented to the user. The user interface 102 can include a three-dimensional model of at least a portion of a subject's anatomy. In various embodiments, the three-dimensional model can include a representation of a brain 112 as shown in FIG. 1. However, applications herein are not limited only to the brain and, in some embodiments, the user interface can include a three-dimensional model of one or more tissues, including heart, pancreas, lungs, liver, uterus, ovaries, stomach, prostate gland, kidney, thyroid, bladder, and intestines. Other tissue types may also be present in a three-dimensional visualization system, including blood vessels, lymph vessels, bone, nervous tissue, and connective tissue.

Within a given organ or organ structure, tissue substructures and subtypes can be represented. For example, in the brain, grey matter, white matter, ventricles, and the like, can be represented. As another example, in the kidney, the cortex, medulla, collection ducts, and the like can be discriminated.

In various embodiments, the user interface 102 can also include and/or be used to model contrast enhanced volumes/regions/zones of a subject's anatomy.

The three-dimensional model can extend in the X, Y and Z dimensions and can be manipulated by a user to alter the vantage point on the user interface 102. The user interface 102 can also include various interactive menu bars, radio buttons, form fields, toggle switches, and the like.

The medical visualization system 100 can be configured to present the three-dimensional model using medical imaging data obtained from a subject or as based on data from a population of subjects. It will be appreciated that the three-dimensional model of the subject's anatomy can be generated using a variety of sources of data, including subject data gathered in real-time, previously stored subject data (such as data stored in files, folders, and/or databases), and idealized model data. Subject data gathered in real-time can include data such as medical imaging data including, but not limited to, x-ray radiography data, fluoroscopy data, computerized axial tomography (CAT) data, magnetic resonance imaging (MRI) data, camera data, and the like. Previously stored subject data can include data such as medical imaging data including, but not limited to, x-ray radiography data, fluoroscopy data, computerized axial tomography (CAT) data, magnetic resonance imaging (MRI) data, camera data, and the like.

In some embodiments idealized model data can be used for visualization and include idealized models of anatomical structure, including, but not limited to, major organs (heart, lungs, liver, kidneys, brain, etc.), joints, bone structure, musculature, chest cavity, the vascular system, central and peripheral venous systems, the cardiopulmonary system, the lymphatic system, the hepatic system, the renal system, the head and the brain, sinuses, etc. and/or medical devices used in medical procedures including, but not limited to, implants, heart valves, embolic protection devices, stents, grafts, medical instruments, cardiac rhythm management devices, pacemakers, implantable cardioverter defibrillators, cardiac resynchronization therapy devices, ventricular assist devices, and the like. Idealized model data can be stored in CAD file formats including information regarding geometry (wireframe, surface, solid, etc.) or can be stored in other file formats including similar information about the idealized models. It will be appreciated that idealized model data can include data obtained from population-level data of a representative group of age-matched, sex-matched, and sized-matched individuals. In some embodiments, the idealized model data can be generated from averaged population-level data.

The medical visualization system 100 can be configured to use the three-dimensional model and calculate the placement of at least one cancer therapy stimulation lead to be used in a treatment of a medical condition. As part of the calculations, the medical visualization system can assign electrical properties to the tissue types of the three-dimensional model. For example, the medical visualization system can assign an electrical property to healthy tissue, a cancerous tissue, and various critical structures. As used herein, the term "critical structures" can refer to various tissues, including one or more of bone, nerves, pituitary gland, blood vessels, hypothalamus, brain ventricles, brain stem, amygdala, thalamus, cerebellum, or corpus callosum. The electrical property values for the healthy tissue, cancerous tissue, and critical structures can be referenced using a lookup table of expected scenarios or can be obtained by performing a calculation based on the type of tissue identified by the three-dimensional model.

Using the assignments of respective tissue types, the medical visualization system 100 can calculate and identify the optimal placement of at least one therapy stimulation lead in a subject's anatomy to treat a medical condition or otherwise provide therapy within the subject. Medical conditions treated and/or therapies can include, but are not limited to, treatment of tumor resection sites, zones, or cavities to prevent recurrence of a cancer, treatment of tumors, cancerous tumors, pre-cancerous lesions, zones, or tissues areas of concern or at risk, or other cancers or related conditions. Beyond cancer, medical conditions treated herein can include dystonia, epilepsy, a cancerous tumor, obsessive-compulsive disorder, or Parkinson's disease.

In various embodiments, the medical visualization system 100 can be configured to calculate the placement of at least one cancer therapy stimulation lead by avoiding one or more critical structures present in the three-dimensional model of the subject's anatomy. A critical structure can include any portion of the subject's anatomy that could be damaged or present decreased functionality if disrupted by a foreign object. For example, the medical visualization system can be configured to determine placement of at least one cancer therapy stimulation lead to avoid various critical structures including bone, nerves, blood vessels, pituitary gland, hypothalamus, brain ventricles, brain stem, amygdala, thalamus, cerebellum, or corpus callosum. In various embodiments, the medical visualization system can be configured to calculate the placement of at least one cancer therapy stimulation lead to both treat the condition of the subject and avoid one or more critical structures.

The medical visualization system 100 can be configured to calculate not only the position of at least one cancer therapy stimulation lead, but also the number of cancer therapy stimulation leads required, the number of electrodes required to be on each cancer therapy stimulation lead, and the pattern and timing of duty cycling of the electrodes. Exemplary cancer therapy stimulation leads are disclosed in commonly owned U.S. Pat. Appl. No. 63/298,528, the content of which is hereby incorporated by reference in its entirety.

Figure 2:
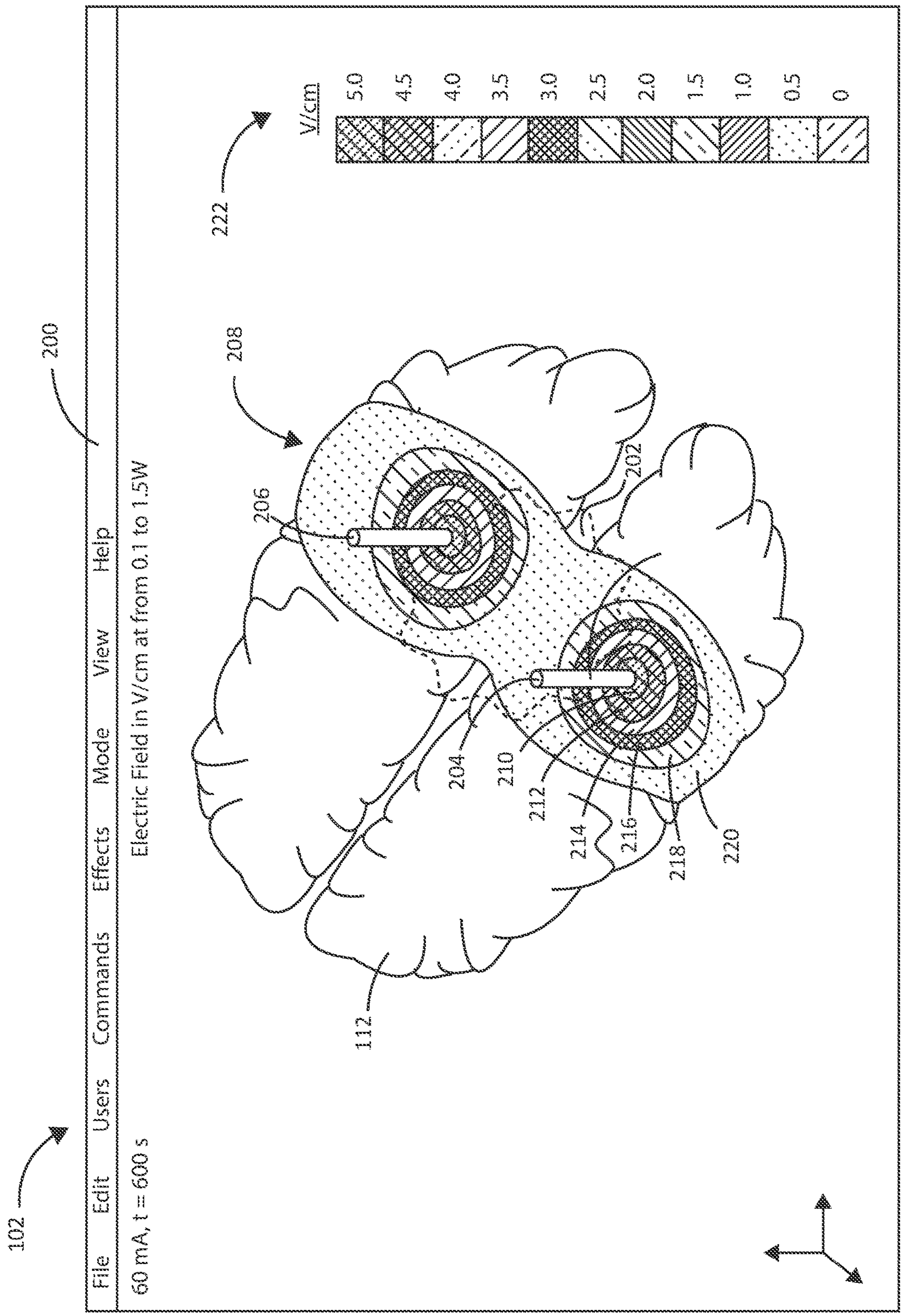
FIG. 2 is a schematic view of a user interface illustrating an electric field strength zone in accordance with various embodiments herein.

The medical visualization system herein can be configured to model an electric field strength zone associated with cancer therapy stimulation leads, which can be used to further refine placement of the cancer therapy stimulation leads. In general, the field in an area or region can be estimated at any point in time based on the active electrodes. Referring now to FIG. 2, a schematic view of a user interface 102 illustrating a graphic representation of an electric field strength zone is shown in accordance with various embodiments herein. The user interface 102 can include a three-dimensional model of at least a portion of a subject's anatomy, such as the brain 112. The three-dimensional model of the subject's anatomy can also include a cancerous tumor 202 (shown as a dotted line in FIG. 2). In various embodiments, the user interface 102 can include a menu bar 200 that includes various interactive menu options such as, but not to be limited to, File, Edit, Users, Commands, Effects, Mode, View, Help, and the like.

The user interface 102 can display a graphic representation of at least one cancer therapy stimulation lead positioned within the three-dimensional model of the subject's anatomy at a treatment site. In the embodiment shown in FIG. 2, two cancer therapy stimulation leads 204 and 206 are present on opposing sides of a targeted area for treatment such as a cancerous tumor 202. In various embodiments herein, the illustrated area of the cancerous tumor 202 can instead represent a tumor resection site or zone. While FIG. 2 shows two cancer therapy stimulation leads, it will be appreciated that in some embodiments, the user interface 102 can display from 1 to 5 cancer therapy stimulation leads. In various embodiments, the user interface 102 can display 1, 2, 3, 4, or 5 cancer therapy stimulation leads. In various embodiments, more than 5 cancer therapy stimulation leads can be used.

The medical visualization system herein can be configured to provide optimal placement of one or more cancer therapy stimulation leads and can provide a graphic representation of an electric field zone overlaid at the site of lead placement on the three-dimensional model. FIG. 2 includes a graphic representation of electric field strength zone 208 as associated with cancer therapy stimulation leads 204 and 206. The graphic representation of the electric field strength zone 208 can include one or more gradients of electric field strengths as represented by electric field strengths 210, 212, 214, 216, 218, and 220 that decrease in intensity in a radial direction away from the center of the cancer therapy stimulation lead 204. It will be appreciated each cancer therapy stimulation therapy lead in the graphic representation can include an electric field strength gradient. In various embodiments, each cancer therapy stimulation therapy lead can include the same electric field strength gradient. In various other embodiments, each cancer therapy stimulation therapy lead can include a different electric field strength gradient.

An electric field strength scale 222 including values for electric field strengths can be included in the user interface 102 as a legend to identify a value for the electric field strengths depicted on the display. While the electric field strengths in FIG. 2 are represented as discrete regions within the electric field strength zone 208, it will be appreciated that electric field strength can decrease in strength in a radial direction away from the center of the cancer therapy stimulation leads in a diffuse gradient (or continuous gradient) rather than in discrete circular regions (or stepped gradient). It will further be appreciated that in some embodiments, there will be overlap between electric field strength zones centered on one or more cancer therapy stimulation leads, as will be discussed in more detail below with respect to FIGS. 7-12. In various embodiments, the overlapping electric field strength zones can lead to an increase in electric field strength greater than an electric field strength zone without overlap. It will be appreciated, however, that the nature of field increase is not, in many cases, merely a matter of looking at the intersection of individual field gradients. However, embodiments herein can determine the actual shapes of field enhancement using various techniques as described herein.

In various embodiments, the electric field strengths modeled by the medical visualization system can be calculated using a variety of methods. In some embodiments, the medical visualization system can calculate the local electric field strength of the treatment site as the quotient $E=J/\sigma$ where J is the current density of the tissue at the treatment site and $\sigma$ is the tissue conductivity. In some embodiments, the medical visualization system can calculate the average electric field strength at the treatment site as the quotient $E=I/A\sigma$ where I is the current of the stimulation lead, A is the active electrode area, and $\sigma$ is the tissue conductivity. For regions proximal to the stimulation leads, the electric field strength can be approximated as $E \approx I/A(R_2/R_1)\sigma$ where I is the current of the stimulation lead, A is the active electrode area, $R_2$ is the radial distance from the stimulation lead surface, $R_1$ is the radius of the stimulation lead, and $\sigma$ is the tissue conductivity. In some embodiments, to measure at greater distances (such as further than a few diameter from the stimulation lead or further than a few centimeters), traditional finite element methods (FEM), model-based estimates, and/or lookup tables may be used to calculate the electric field strength.

In various embodiments, the electric field strengths modeled by the medical visualization system can include those from 0 volts per centimeter (V/cm) to 70 V/cm, or 0 volts per centimeter (V/cm) to 25 V/cm, or 0 volts per centimeter (V/cm) to 10 V/cm, or 0 volts per centimeter (V/cm) to 5 V/cm. In some embodiments, the electric field strength can be greater than or equal to 0 V/cm, 0.01 V/cm, 1 V/cm, 2 V/cm, 3 V/cm, 4 V/cm, 5 V/cm, 7.5 V/cm, 10 V/cm, 15 V/cm, 20 V/cm, 30 V/cm, 40 V/cm, 50 V/cm, 60 V/cm, or 70 V/cm, or can be an amount falling within a range between any of the foregoing.

The electric field strengths described herein can be modeled at a delivery power of from 0.1 watts (W) to 20 W or more, 0.1 watts (W) to 15 W, 0.1 watts (W) to 10 W, watts (W) to 7.5 W, 0.1 watts (W) to 5 W, 2 watts (W) to 5 W, or the like. In some embodiments, the electric field strengths described herein can be modeled at a delivery power that can be greater than or equal to 0.10 W, 0.35 W, 0.60 W, 0.85 W, 1.10 W, 1.35 W, 1.50 W, 2 W, 2.5 W, 3 W, 3.5 W, 4 W, 5 W, 7.5 W, 10 W, 12.5 W, 15 W, 17.5 W, 20 W, or can be an amount falling within a range between any of the foregoing.

In some embodiments, the system can be configured to accept user input regarding a zone of interest around a tumor or a surgical tumor resection site. For example, the user input can mark a tumor site or surgical site such as through direct interaction with the user interface with a touch interface, or an input device such as a pen, mouse, or keyboard (or that information can be pre-inserted) and specify a particular distance (such as 0.5, 1, 2, 3, 4, 5, 6, 7, 8, 9, or 10 cm or more, or a number falling within a range between any of the foregoing) and then the calculated field strengths within that zone are displayed by the medical visualization system. In that manner, the system can specifically highlight information regarding field strengths in an area of most interest to the clinician or other system user. In some embodiments, the system can be configured to show gradients of field strength within the zone of interest. In some embodiments, the system can be configured to show areas within the zone of interest where the field strength crosses a threshold value (such as exceeding a minimum threshold value) as set through user input. In some embodiments, the system can be configured such that a user with a therapeutic field strength requirement can select a region of interest (a tumor, a tumor resection border area, a particular anatomical structure, a contrast enhanced region, etc.) and the system can compute parameters necessary for the region of interest to be provided with therapy meeting the therapeutic field strength requirement. A region of interest can be designated through accepting user input such as through a touch screen interface, a pointing device, keyboard commands, or the like. In some embodiments, using proposed electrode and/or lead locations, the system can calculate and/or report out the estimated power needed to achieve a local minimum field or a local average field strength at a given site, zone, or region of interest.

Figure 3:
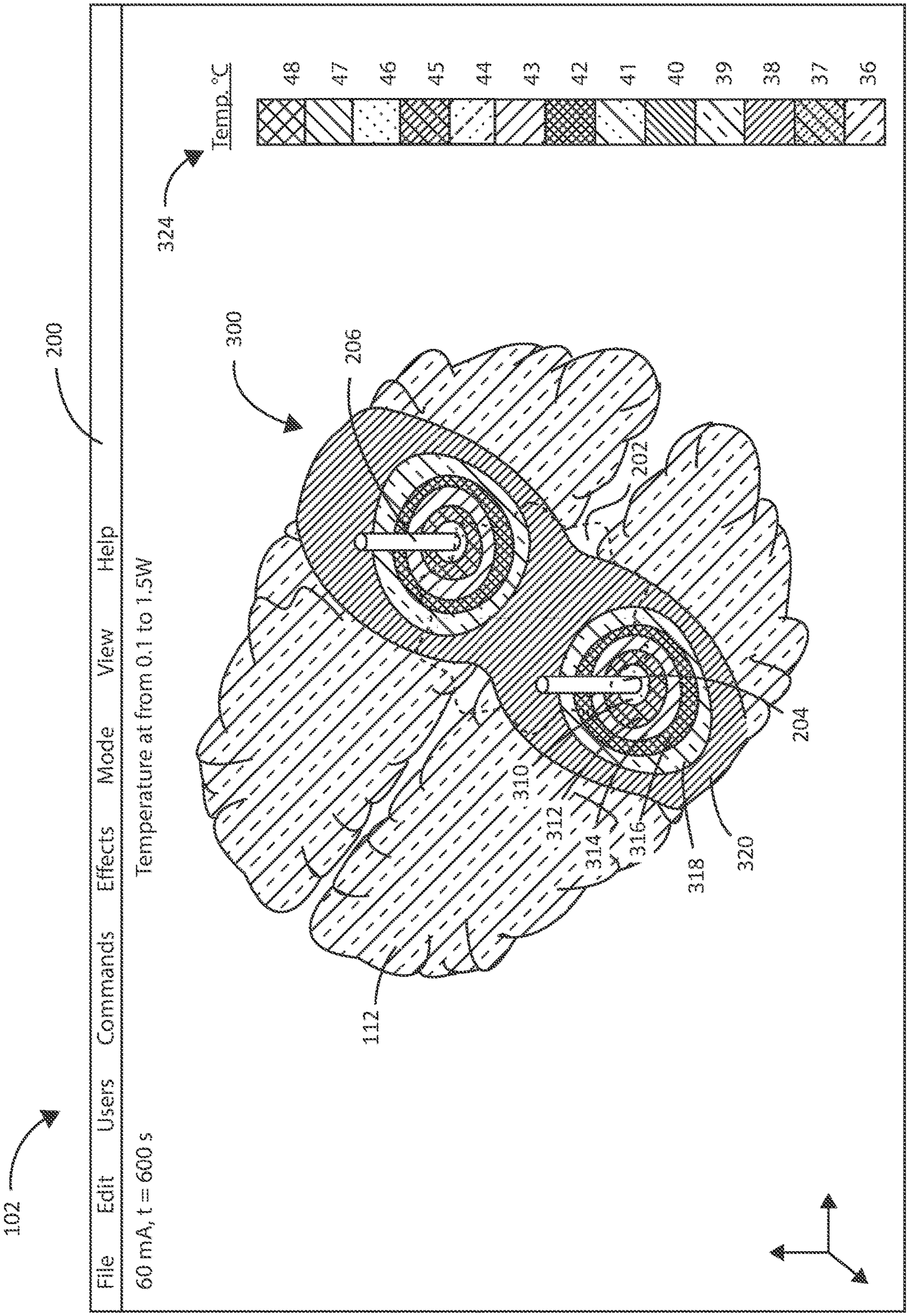
FIG. 3 is a schematic view of a user interface illustrating thermal heating zone in accordance with various embodiments herein.

The medical visualization system herein can also be configured to model a thermal heating zone associated with cancer therapy stimulation leads, in addition to or instead of modeling field strength, which can also be used to further refine placement of the cancer therapy stimulation leads. Referring now to FIG. 3, a schematic view of a user interface 102 illustrating an embodiment of a graphic representation of a thermal heating zone is shown in accordance with various embodiments herein. The user interface 102 can include a three-dimensional model of at least a portion of a subject's anatomy, such as the brain 112. The three-dimensional model of the subject's anatomy can also include a cancerous tumor 202, (shown as a dotted line in FIG. 3). In various embodiments, the user interface 102 can include a menu bar 200 that includes various interactive menu options such as, but not to be limited to, File, Edit, User, Commands, Effects, Mode, View, Help, and the like.

The user interface 102 can display a graphic representation of at least one cancer therapy stimulation lead positioned within the three-dimensional model of the subject's anatomy at a treatment site. In the embodiment shown in FIG. 3, two cancer therapy stimulation leads 204 and 206 are present on opposing sides of cancerous tumor 202. While FIG. 3 shows two cancer therapy stimulation leads, it will be appreciated that in some embodiments, the user interface 102 can display from 1 to 5 cancer therapy stimulation leads. In various embodiments, the user interface 102 can display 1, 2, 3, 4, or 5 cancer therapy stimulation leads. In various embodiments, more than 5 cancer therapy stimulation leads can be used.

The medical visualization system herein can be configured to provide optimal placement of one or more cancer therapy stimulation leads and can provide a graphic representation of a thermal heating zone overlaid at the site of lead placement on the three-dimensional model. FIG. 3 includes a virtual thermal heating zone 300 as associated with cancer therapy stimulation leads 204 and 206. The graphic representation of the thermal heating zone 300 can include one or more gradients of thermal heating that including temperatures 310, 312, 314, 316, 318, and 320 that can decrease in intensity in a radial direction away from the center of the cancer therapy stimulation lead 204. It will be appreciated each cancer therapy stimulation therapy lead in the graphic representation can include a thermal heating zone gradient. In various embodiments, each cancer therapy stimulation therapy lead can include the same thermal heating zone gradient. In various other embodiments, each cancer therapy stimulation therapy lead can include a different thermal heating zone gradient. In various embodiments, each estimation of thermal gradient can be configured to include the parametric contributions of tissue impedance, therapy duty cycle, electrode heat spreading, return electrode, and local thermal impedance as well as other factors that may include diurnal or special cause thermal fluctuations.

A temperature scale 324 can be included in the user interface 102 as a legend to identify a value for the temperatures depicted on the display. While the temperatures in FIG. 3 are represented as discrete regions within the thermal heating zone 300, it will be appreciated that temperature will decrease in strength in a radial direction away from the center of the cancer therapy stimulation leads in a diffuse gradient (or continuous gradient) rather than distinct circular regions (or stepped gradient). It will further be appreciated that in some embodiments, there will be overlap between thermal heating zones centered on one or more cancer therapy stimulation leads, as will be discussed in more detail below with respect to FIGS. 7-12. In various embodiments, the overlapping thermal heating zones can lead to an increase in temperature greater than a thermal heating zone without overlap.

The user interface 102 can display the thermal heating zone around the cancer therapy stimulation leads extending in a radial direction away from a center point of the cancer therapy stimulation leads. In some embodiments, the temperature of the thermal heating zone can be between 36° C. and 48° C. In some embodiments, the temperature can be greater than or equal to 36° C., 37° C., 38° C., 39° C., 40° C., 41° C., 42° C., 43° C., 44° C., ° C., 46° C., 47° C., or 48° C., or can be an amount falling within a range between any of the foregoing.

In various embodiments, the thermal heating zone modeled by the medical visualization system can be approximated using a variety of methods. In some embodiments, the medical visualization system can approximate the thermal heating zone using lookup tables scaled to current tissue density values, duty cycles, tissue type, and geometric data. In some embodiments, the medical visualization system can approximate the thermal heating zone using the electric field strengths calculated in combination with the tissue properties.

The thermal heating zone described herein can be modeled at a delivery power of from 0.1 watts (W) to 20 W or more, 0.1 watts (W) to 15 W, 0.1 watts (W) to 10 W, 0.1 watts (W) to 7.5 W, 0.1 watts (W) to 5 W, 2 watts (W) to 5 W, or the like. In some embodiments, the thermal heating zone described herein can be modeled at a delivery power that can be greater than or equal to 0.10 W, 0.35 W, 0.60 W, 0.85 W, 1.10 W, 1.35 W, 1.50 W, 2 W, 2.5 W, 3 W, 3.5 W, 4 W, 5 W, 7.5 W, 10 W, 12.5 W, 15 W, 17.5 W, 20 W, or can be an amount falling within a range between any of the foregoing.

In some embodiments, the medical visualization system can be configured to allow a user to manipulate a position of one or more cancer therapy stimulation leads and the medical visualization system 100 can recalculate the position and values for the electric field strength zone 208 and the thermal heating zone 300. The user interface 102 can be updated during such a recalculation to display new position data for the cancer therapy stimulation lead(s) as manipulated by the user. The user interface 102 can also be updated during such a recalculation to display new and an updated electrical field strength and/or thermal heating zone information.

In some embodiments, the medical visualization system can be configured to allow a user to mark a point of interest and see the temperature of the thermal heating zone at that point. For example, the system can be configured to allow the user to select a specific point or structure (using, for example, a mouse, a pen input device, a touch screen or the like) and see (such as through a pop-up box or a text field or graphic object) the temperature associated with that particular point of interest or structure.

It will be appreciated, that in various embodiments the medical visualization system can be configured to display both the thermal heating zone and the electric field strength associated with cancer therapy stimulation leads. By having the medical visualization system present both the thermal heating zone and the electric field strengths simultaneously, the user can refine the placement of the stimulation leads for optimal placement using the modeling data associated with the thermal heating zone and the electric field strength. Additionally, the user can visualize how refining the placement of the stimulation leads affects both the thermal heating zone and the electric field strengths.

Figure 4:
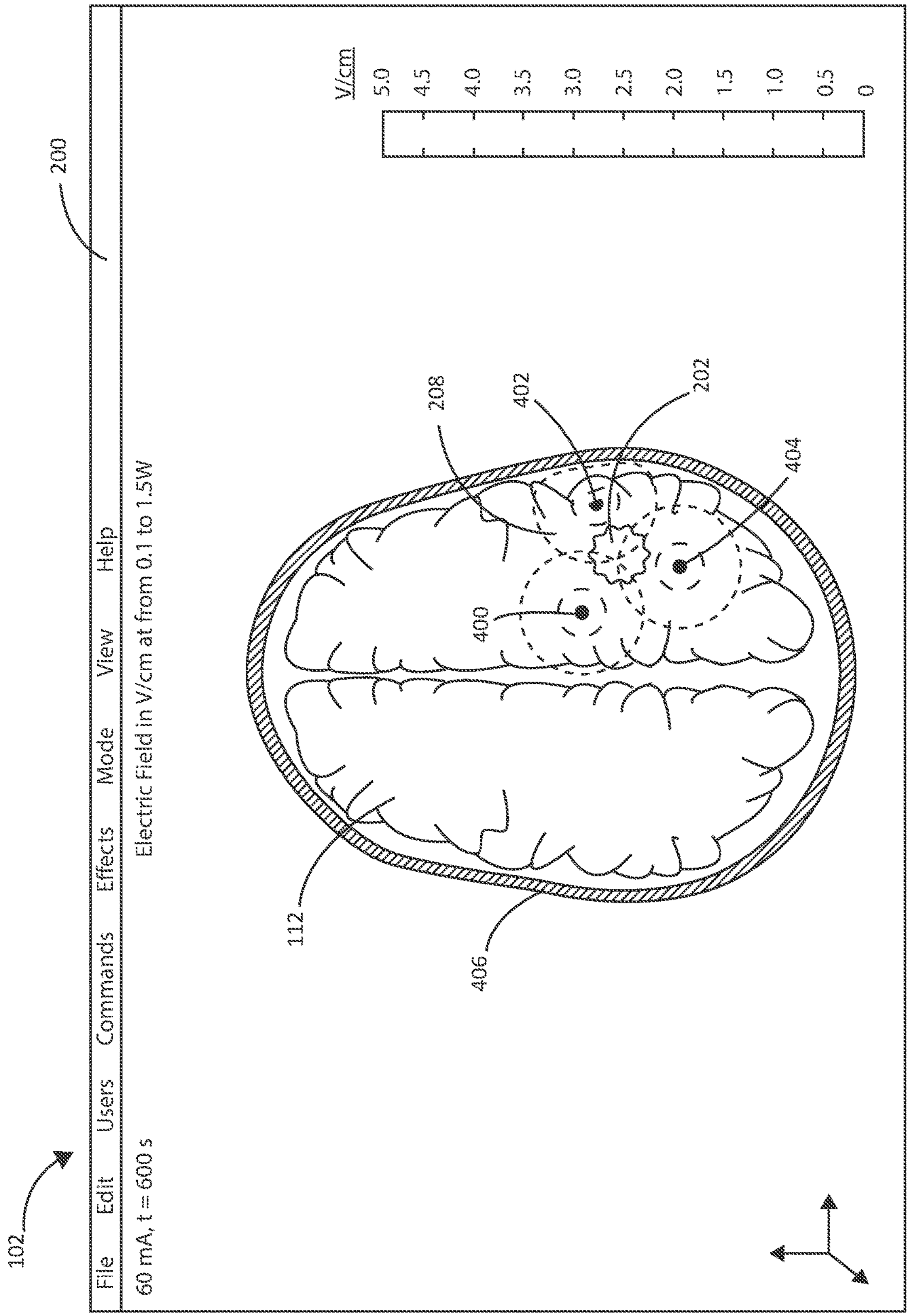
FIG. 4 is a schematic view of a user interface illustrating placement of various cancer therapy stimulation leads in accordance with various embodiments herein.

The medical visualization system 100 can be configured to present the three-dimensional model on user interface with multiple cancer therapy stimulation leads. Referring now to FIG. 4, a schematic view of a user interface 102 illustrating an embodiment with the placement of cancer therapy stimulation leads 400, 402, and 404 is shown in accordance with various embodiments herein. The user interface 102 can include interactive features as described above in reference to FIGS. 2 and 3. The user interface 102 can include a portion of a three-dimensional representation of a subject's anatomy, including brain 112 and skull 406.

As described above, the medical visualization system can calculate an optimal placement of one or more cancer therapy stimulation leads and the user interface 102 can display the position of the cancer therapy stimulation leads along with any corresponding electric field strengths (indicated by the dotted lines surrounding each cancer therapy stimulation lead 400, 402, and 404). In some embodiments, the medical visualization system can calculate an optimal placement of the cancer therapy stimulation leads 400, 402, and 404 around a cancerous tumor 202. In other embodiments, such as illustrated with regard to FIG. 18 herein, the medical visualization system can calculate an optimal placement of the cancer therapy stimulation leads 400, 402, and 404 within or around a tumor resection site or cavity.

In some embodiments, the cancer therapy stimulation leads 400, 402, and 404 can be positioned in a region containing the cancerous tumor 202. In some embodiments, the cancer therapy stimulation leads 400, 402, and 404 can be positioned about a center point of the cancerous tumor 202. In other embodiments, the cancer therapy stimulation leads 400, 402, and 404 can be positioned about a non-centered point of the cancerous tumor 202. In some embodiments, the cancer therapy stimulation leads can be positioned about the circumference of the cancerous tumor In various embodiments, the cancer therapy stimulation leads herein can be placed at from 70 degrees to 120 degrees apart from one another relative to the center point of the cancerous tumor 202. In various embodiments, the cancer therapy stimulation therapy leads can be positioned apart from one another around a cancerous tumor at from greater than or equal to 70 degrees, 80 degrees, 90 degrees, 100 degrees, 110 degrees, 120 degrees, 130 degrees, 140 degrees, 150 degrees, 160 degrees, 170 degrees, or 180 degrees, about a cancerous tumor relative to one another, or can be an amount falling within a range between any of the foregoing. By way of example, the cancer therapy stimulation leads 400, 402, 404 in FIG. 4 are shown to be positioned at 120 degrees, about the center point of the cancerous tumor 202. In some embodiments the cancer therapy stimulation leads can be spaced equally about center point of the cancerous tumor. In other embodiments, the cancer therapy stimulation leads can be spaced unequally about the center point of the cancerous tumor. In various embodiments, one or more cancer therapy stimulation leads can be positioned within the cancerous tumor.

Figure 5:
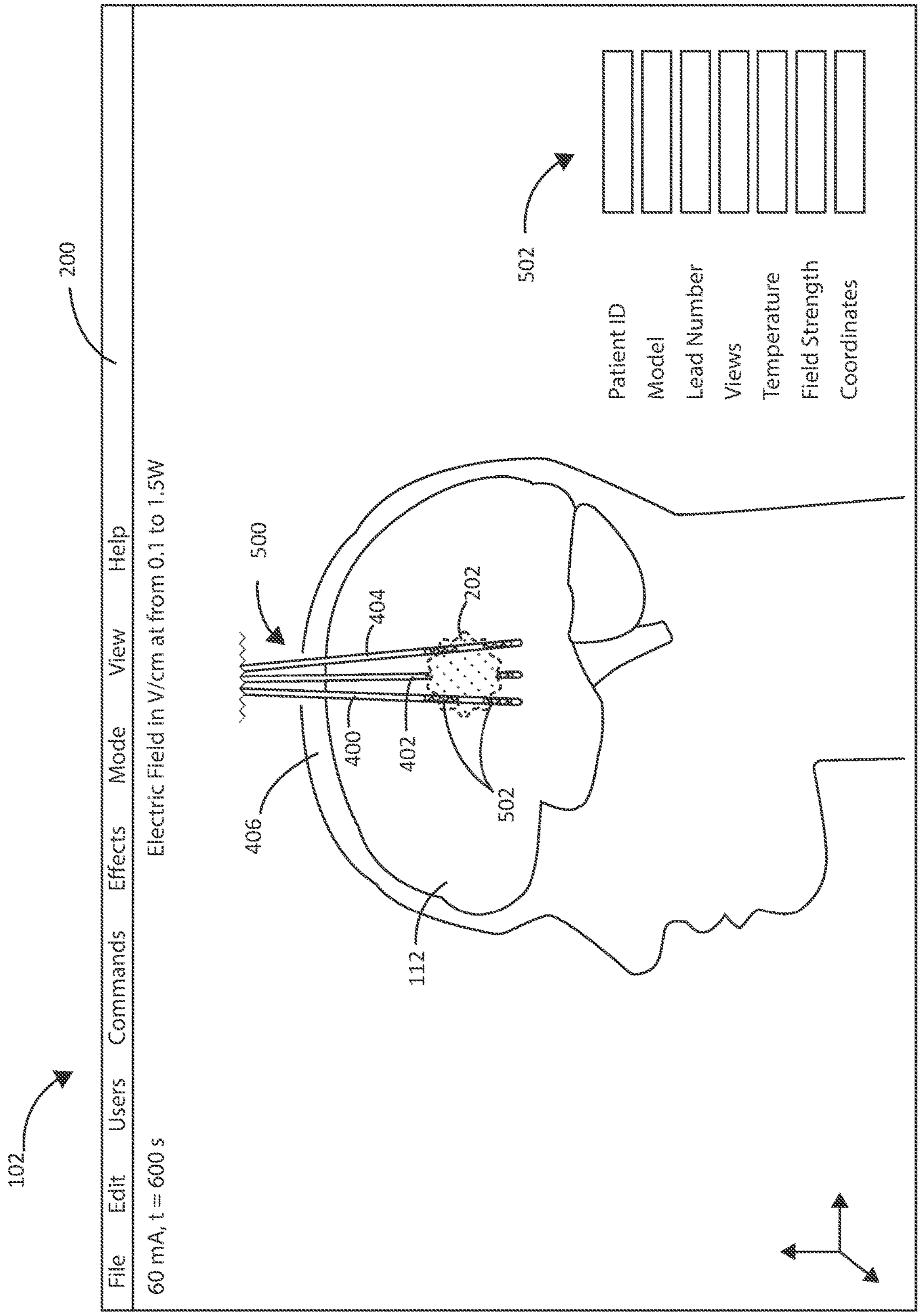
FIG. 5 is a schematic view of a user interface illustrating placement of various cancer therapy stimulation leads in accordance with various embodiments herein.

In some embodiments, the user interface 102 can be configured to display a top down or birds eye view of the three-dimensional model. Alternatively, the user interface 102 can be configured to display a side view of the three-dimensional model or a perspective view. Referring now to FIG. 5, a schematic view of a user interface 102 illustrating an embodiment of a placement of cancer therapy stimulation leads shown in accordance with various embodiments herein. In the embodiment shown in FIG. 5, the user interface 102 includes a side view of cancer therapy stimulation leads 400, 402, and 404, where each cancer therapy stimulation lead includes two electric field generating electrodes 502 disposed along a length of the cancer therapy stimulation leads. Each cancer therapy stimulation lead includes a proximal and a distal electric field generating electrode. It will be appreciated that each cancer therapy stimulation lead can include one or more electric field generating electrodes. Cancer therapy stimulation leads and the electric field generating electrodes disposed thereon are discussed in more detail below.

The side view shown in FIG. 5 also includes the placement of cancer therapy stimulation leads 400, 402, and 404 around a cancerous tumor 202 and in position within a burr hole 500 entry point on the subject's skull 406. The medical visualization system can be configured to utilize the three-dimensional model of the subject's anatomy to provide placement of one or more burr holes within a subject's skull to optimize placement of one or more cancer therapy stimulation leads at a cancerous tumor within the brain. It will be appreciated that in some embodiments one burr hole can be used with one or more (e.g., one, two, three, or more) leads and/or electrodes. In some embodiments, multiple burr holes can be used each with one or more (e.g., one, two, three, or more) leads and/or electrodes.

In various embodiments, the user interface 102 can also include biographical and biometric data, which can include personal information and device information, such as identification number, a device model number, the number of a cancer therapy stimulation leads in the user interface, the point of view of the user interface, the temperature of the cancer therapy stimulation leads, the electric field strength of the cancer therapy stimulation leads, and the coordinates of the cancer therapy stimulation leads.

Figure 6:
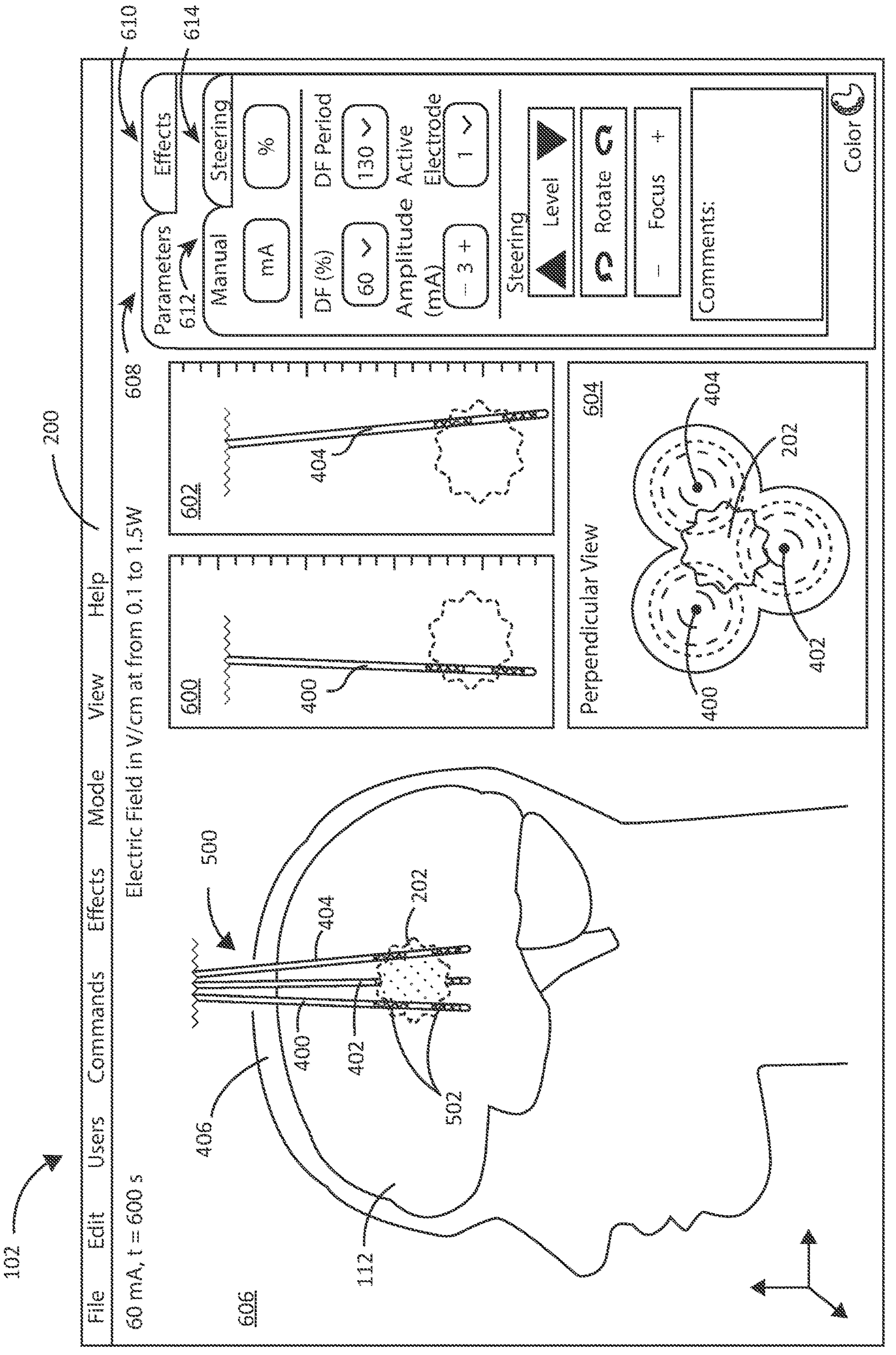
FIG. 6 is a schematic view of a user interface illustrating multiple views of the placement of cancer therapy stimulation leads in accordance with various embodiments herein.

In various embodiments, the user interface 102 can display multiple views of a treatment at once. Referring now to FIG. 6, a schematic view of a user interface 102 illustrating multiple views of the placement of cancer therapy stimulation leads is shown in accordance with various embodiments herein. The user interface 102 can include all features of the side view as shown in FIG. 5. The user interface 102 can also include various zoomed views 600 and 602. Zoomed view 600 can include a more detailed view of cancer therapy stimulation lead 400 and its placement in a treatment area. Zoomed view 602 can include a more detailed view of cancer therapy stimulation lead 404 and its placement in a treatment area. It will be appreciated that the user interface 102 can be configured to toggle between any number of the cancer therapy stimulation leads 400, 402, and 404. The user interface 102 can also include a perpendicular view 604 that includes features of the of the main view 606 rotated 90 degrees relative to the main view 606.

The user interface 102 can include various interactive command interface objects including tabs 608, 610, 612 and 614. The command interface objects can include various elements that a user can interact in the user interface 102 to manipulate views, change parameters, and add various effects. Command interface objects can include, but are not limited to, a button, a menu tree, a menu bar, a ratio button, a slider bar, a dial, a pointer, a cursor, and the like. For example, a user can manipulate the three-dimensional model using a user interface device such as a keyboard and/or mouse that can be used to interact with the various command interface objects. Engagement or actuation of the command interface objects by the user can cause various actions or functions to be executed on the user interface 102.

The user interface 102 can be configured to be manipulated by a user such that various visualization components can be turned off or on. Visualization components can include the subject's anatomy, including brain 112, skull 406, cancerous tumor 202, cancer therapy stimulation leads 400, 402, and 404, and various critical structures. For example, a user could turn off portions of the subject's anatomy, including brain 112 and skull 406 while leaving on the cancerous tumor 202 and cancer therapy stimulation leads 400, 402, and 404. Alternatively, the user could turn off the subject's anatomy and the cancerous tumor 202 while leaving on the cancer therapy stimulation leads 400, 402, and 404 and any critical structures that may be present. In some embodiments, the user interface 102 can allow for a user to quickly navigate between various views with different visualization components turned on and off.

Figure 7:
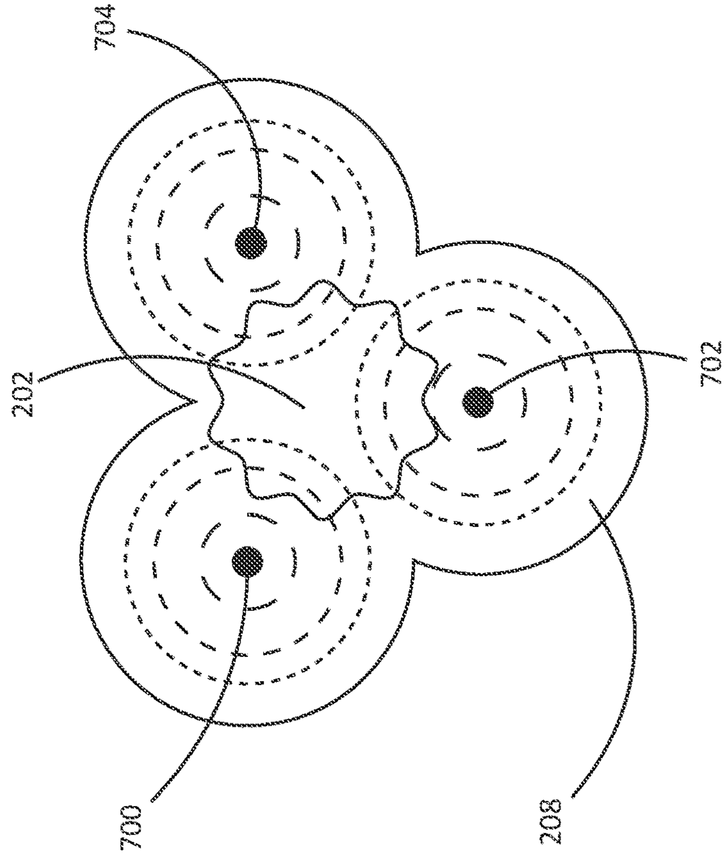
FIG. 7 is a top view of a graphic representation of a placement of various cancer therapy stimulation leads in a region of a cancerous tumor in accordance with various embodiments herein.

FIGS. 7-12 include exemplary cancer therapy stimulation lead placements where various numbers of cancer therapy stimulation leads are shown positioned within a region of a cancerous tumor or a tumor resection site or zone. Referring now to FIG. 7, a top view of a graphic representation of a placement of three cancer therapy stimulation leads in a region of a cancerous tumor is shown in accordance with various embodiments herein. Cancer therapy stimulation leads 700, 702, and 704 can be positioned around a center point of the cancerous tumor 202 (or tumor resection site) at approximately 120 degrees apart from each other. Each cancer therapy stimulation lead can be modeled to generate an electric field strength zone 208 around the circumference of the lead. In various embodiments, each of the cancer therapy stimulation leads 700, 702, and 704 can include an electric field strength zone 208 that can overlap at least a portion of the cancerous tumor 202 or tumor resection site. In various embodiments, each of the cancer therapy stimulation leads 700, 702, and 704 can include an electric field strength zone 208 that can overlap a neighboring electric field strength zone 208.

Figure 8:
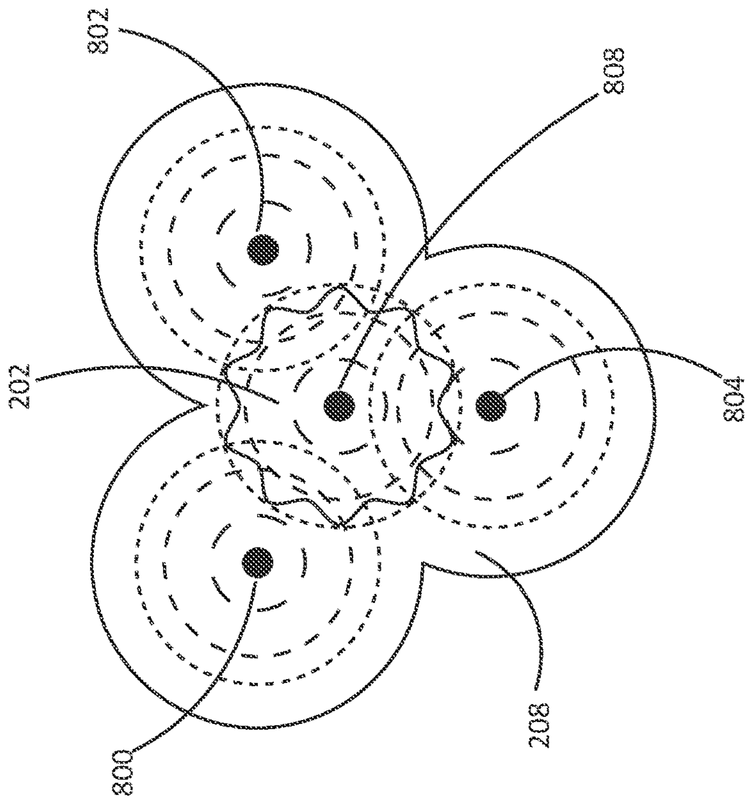
FIG. 8 is a top view of a graphic representation of a placement of four cancer therapy stimulation leads in a region of a cancerous tumor in accordance with various embodiments herein.

Referring now to FIG. 8, a top view of a graphic representation of a placement of four cancer therapy stimulation leads in a region of a cancerous tumor is shown in accordance with various embodiments herein. Cancer therapy stimulation leads 800, 802, and 804 are positioned around a center point of the cancerous tumor 202 (or tumor resection site) at approximately 120 degrees apart from each other. Each cancer therapy stimulation lead can be modeled to generate an electric field strength zone 208 around the circumference of the lead. In various embodiments, each of the cancer therapy stimulation leads 800, 802, and 804 can include an electric field strength zone 208 that can overlap at least a portion of the cancerous tumor 202 or tumor resection site. In various embodiments, each of the cancer therapy stimulation leads 800, 802, and 804 can include an electric field strength zone 208 that can overlap a neighboring electric field strength zone 208. Additionally, in the embodiment shown in FIG. 8, a fourth cancer therapy stimulation lead 808 can be positioned within the cancerous tumor 202 or tumor resection site.

Figure 9:
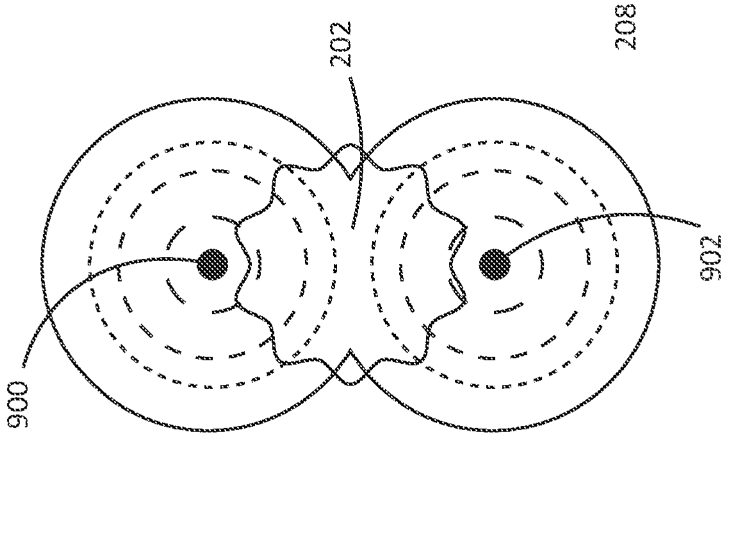
FIG. 9 is a top view of a graphic representation of a placement of two cancer therapy stimulation leads in a region of a cancerous tumor in accordance with various embodiments herein.

Referring now to FIG. 9, a top view of a graphic representation of a placement of two cancer therapy stimulation leads in a region of a cancerous tumor is shown in accordance with various embodiments herein. Two cancer therapy stimulation leads 900 and 902 can be positioned around a center point of the cancerous tumor 202 at approximately 180 degrees apart from each other. such that the electric field strength zone 208 of both of the cancer therapy stimulation leads 900 and 902 overlap. Each cancer therapy stimulation lead can be modeled to generate an electric field strength zone 208 around the circumference of the lead. In various embodiments, each of the cancer therapy stimulation leads 900 and 902 can include an electric field strength zone 208 that can overlap at least a portion of the cancerous tumor 202 or tumor resection site. In various embodiments, each of the cancer therapy stimulation leads 900 and 902 can include an electric field strength zone 208 that can overlap a neighboring electric field strength zone 208.

Figure 10:
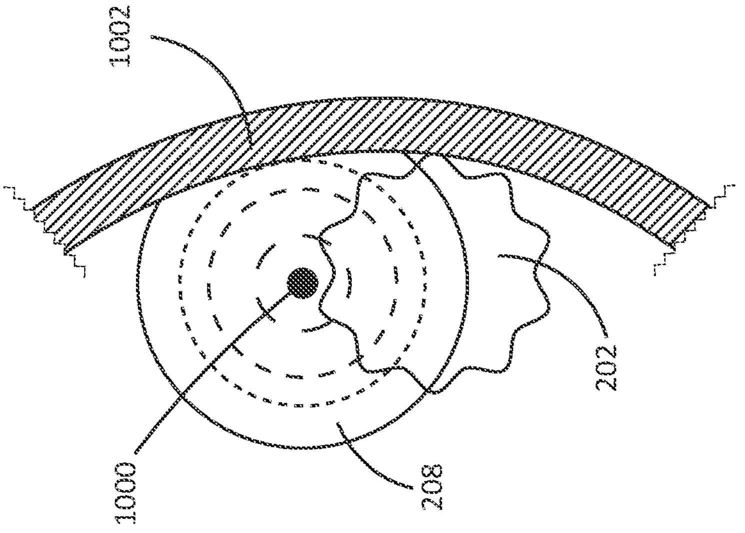
FIG. 10 is a top view of a graphic representation of a placement of a cancer therapy stimulation lead in a region of a cancerous tumor in accordance with various embodiments herein.

Referring now to FIG. 10, a top view of a graphic representation of a placement of a single cancer therapy stimulation lead in a region of a cancerous tumor is shown in accordance with various embodiments herein. Cancer therapy stimulation lead 1000 can be positioned in the region of the cancerous tumor 202 or tumor resection site. In various embodiments, a portion of electric field strength zone 208 generated by cancer therapy stimulation lead overlaps with the portion of the subject's bone 1002. The medical visualization system can be configured to accept input from a user to change the positioning of the cancer therapy stimulation lead 1000 by moving it away from the portion of the subject's bone 1002. Alternatively, the medical visualization system 100 could provide a notification to a user that the cancer therapy stimulation lead 1000 is adjacent to the portion of the subject's bone 1002, allowing for a user to interact with the system to reposition the cancer therapy stimulation lead 1000 as needed. The use of notifications by the medical visualization system herein are described in more detail below.

Figure 11:
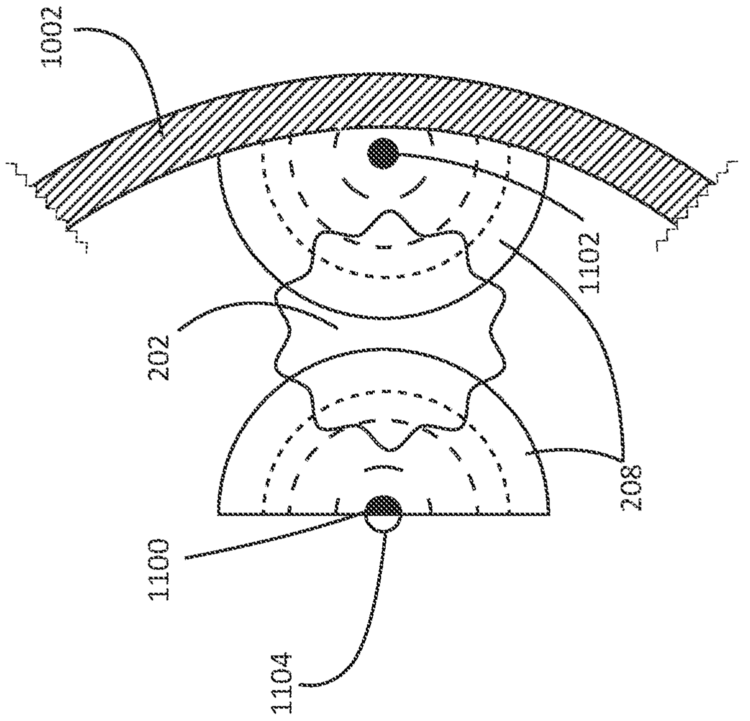
FIG. 11 is a top view of a graphic representation of a placement of two cancer therapy stimulation leads in a region of a cancerous tumor in accordance with various embodiments herein.

Referring now to FIG. 11, a top view of a graphic representation of a placement of two cancer therapy stimulation leads in a region of a cancerous tumor 202 is shown in accordance with various embodiments herein. Cancer therapy stimulation leads 1100 and 1102 can be positioned in the region of the cancerous tumor 202. Cancer therapy stimulation lead 1102 can be positioned adjacent a portion of the subject's bone 1002. In various embodiments, cancer therapy stimulation lead can include one or more insulated or partially insulated directional electric field generating electrodes, such as an insulated or partially insulated electric field generating electrode 1104 to manipulate the electric field strength zone 208 in a direction away from healthy tissue and toward the cancerous tumor 202 or tumor resection site. In various embodiments, an insulated electric field generating electrode can be presented by the medical visualization system to show an induced directionality of a field strength. It will be appreciated that the impact of insulated or partially insulated directional electrodes scales with the dimension. Generally, small diameter electrodes will have small effects. In various embodiments, the system can also model the effect of the longitudinal segmentation of electrodes. For example, the system can model the effects of different amounts of longitudinal segmentation of electrodes to visualize and enable a user to manipulate field distribution.

In various embodiments, at least one electrode can include a shield (such as one shielding electrical fields and/or heat), where the shield can be configured to shape an electric field generated by the electric field generating electrodes. The shield can be in the form of an insulative material or a separate component. By way of example, an electric field shaping element (not shown) can be implanted along with the cancer therapy stimulation lead 1102, where the electric field shaping element can be configured to shape the electric field strength zone 208 and direct it away from the subject's bone 1002 and toward the cancerous tumor 202. Exemplary electric field shaping elements are disclosed in commonly owned U.S. Publ. No. 2019/0117972 filed on Oct. 22, 2018, and which is hereby incorporated by reference in its entirety.

Figure 12:
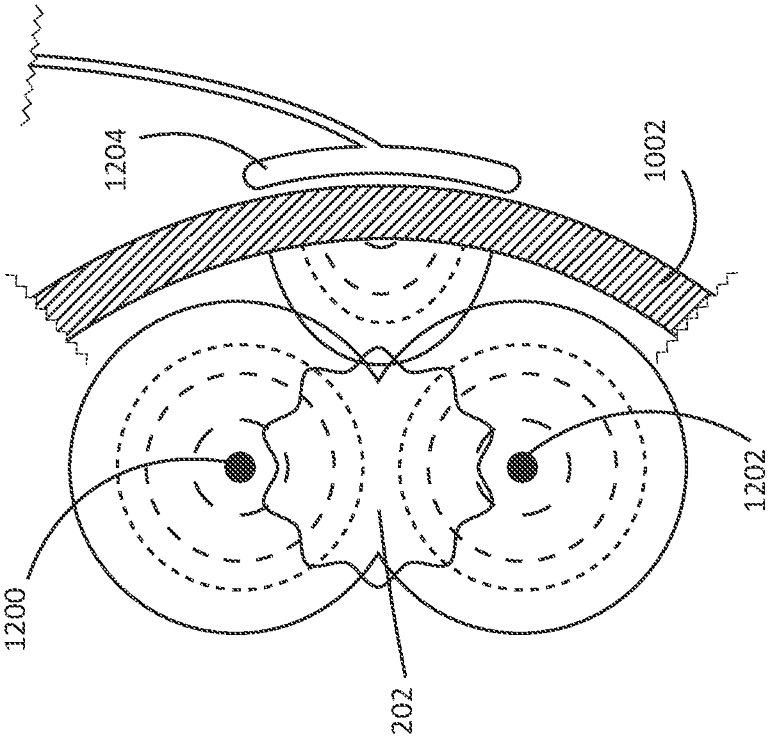
FIG. 12 is a top view of a graphic representation of a placement of two cancer therapy stimulation leads and a subcutaneous electrode in a region of a cancerous tumor in accordance with various embodiments herein.

Referring now to FIG. 12, a top view of a graphic representation of a placement of two cancer therapy stimulation leads and an accessory electric field generating electrode in a region of a cancerous tumor is shown in accordance with various embodiments herein. Cancer therapy stimulation leads 1200 and 1202 are positioned in the region of the cancerous tumor 202 or tumor resection site. An additional accessory electric field generating electrode 1204 can be positioned on the opposite side of the subject's skull in the region of the cancerous tumor 202 or tumor resection site to provide a supplemental electric field strength zone 208 to a treatment site where a supplemental electric field strength zone is needed or where a tumor may otherwise be difficult to reach. It some embodiments, the accessory electric field generating electrode 1204 can be positioned subcutaneously. In various embodiments, the accessory electric field generating electrode 1204 can be positioned transcutaneously. In other embodiments, the accessory electric field generating electrode 1204 can be positioned externally, such as in the context of a patch type electrode. In some embodiments herein, leads may even be omitted and all of the electrodes may be external, such as in the context of patch type electrodes. In some embodiments, some of the electrodes can be implanted (on a lead or otherwise) and some of the electrodes can be external. In some embodiments all of the electrodes can be internal (on a lead or otherwise).

Figure 13:
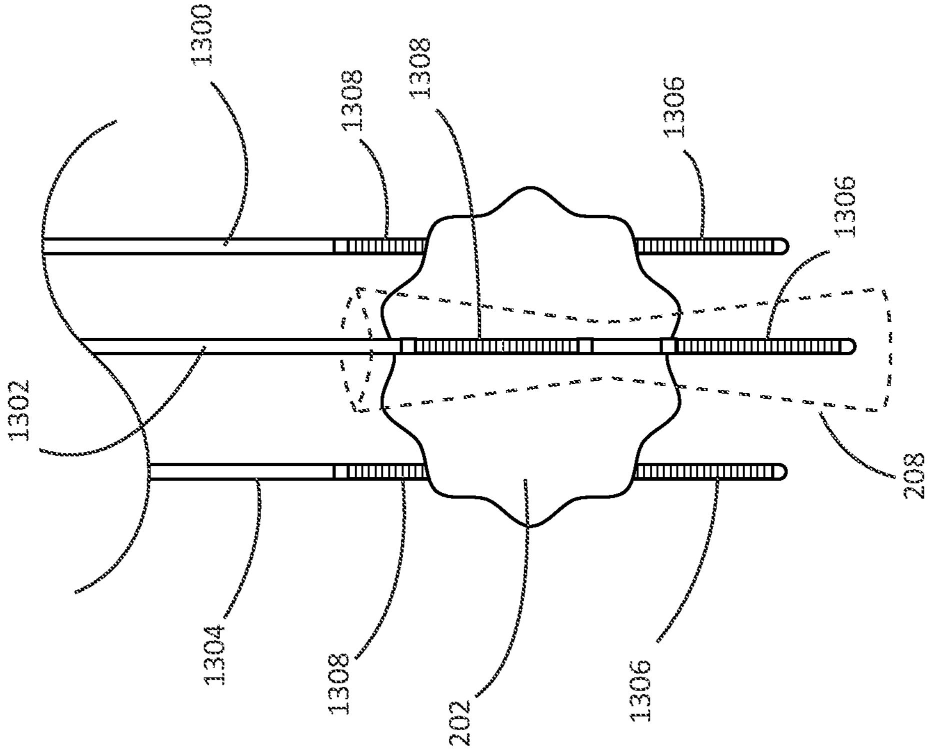
FIG. 13 is a schematic view of a graphic representation of a placement of various cancer therapy stimulation leads in a region of a cancerous tumor in accordance with various embodiments herein.

Referring now to FIG. 13, a schematic view of a graphic representation of a placement of various cancer therapy stimulation leads in a region of a cancerous tumor is shown in accordance with various embodiments herein. Each of the cancer therapy stimulation leads 1300, 1302, and 1304 include two electric field generating electrodes (e.g., a proximal electrode 1306 and a distal electrode 1308). However, it will be appreciated that in some embodiments a greater or lesser number of electrodes can be used. In some embodiments, each of the cancer therapy stimulation leads 1300, 1302, and 1304 can include a different number of electrodes from one another. By way of example, each cancer therapy stimulation lead can include one electrode, two electrodes, or a combination thereof. The cancer therapy stimulation leads 1300, 1302, and 1304 are arranged to be in proximity to the cancerous tumor 202 or tumor resection site. The electric fields can be visualized through the coil electrodes along various stimulation vectors (a pathway through the tissue/tumor interconnecting two different electrodes).

Each cancer therapy stimulation lead 1300, 1302, and 1304 can generate an electric field strength zone 208 about the longitudinal axis of the cancer therapy stimulation leads. The electric field strength zone 208 can be shaped like an hourglass, a cylinder, and the like. The electric field strength zone of the cancer therapy stimulation leads can center around the electric field generating electrodes 1306 and 1308.

Cancer Therapy Stimulation Lead

Figure 14:
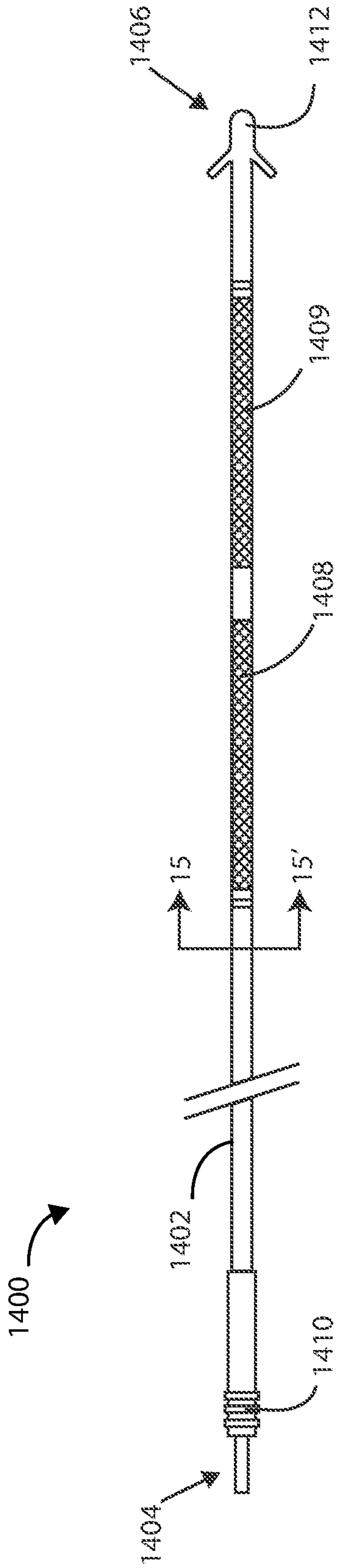
FIG. 14 is a schematic view of a cancer therapy stimulation lead in accordance with various embodiments herein.

Referring now to FIG. 14, a schematic view of a cancer therapy stimulation lead 1400 is shown in accordance with various embodiments herein. The cancer therapy stimulation lead 1400 can include a lead body 1402 with a proximal end 1404 and a distal end 1406. In this example, a first electrode 1408 and a second electrode 1409 are coupled to the lead body 1402, such as positioned near a distal end 1406 thereof. In some embodiments, the electrodes 1408, 1409 can include electric field generating electrodes. In various embodiments, the electrodes 1408, 1409 can include electric field sensing electrodes. The electrodes 1408, 1409 can be internally connected or internally independent. In an example where the electrodes 1408, 1409 are independent, the system herein can model each as an independent field and heat source. The lead body 1402 can define a lumen. The electrodes 1408, 1409 can include various conductive materials such as platinum, silver, gold, iridium, titanium, and various alloys. In some embodiments, the cancer therapy stimulation lead 1400 includes more than two electrodes.

The cancer therapy stimulation lead 1400 can include one or more thermistors disposed along a length of the cancer therapy stimulation lead. The thermistors can be used to measure the thermal heating about the cancer therapy stimulation lead to provide feedback to a clinician about the local thermal heating zone around the lead. In some embodiments, thermistor data can be recorded can then compared with modeled thermal data in order to enhance modeling functions or algorithms to improve the accuracy of thermal modeling.

The cancer therapy stimulation lead 1400 can further include a terminal pin 1410 for connecting the cancer therapy stimulation lead 1400 to an implantable device, such as a cancer treatment device. The terminal pin 1410 can be compatible with various standards for lead-header interface design including the DF-1, VS-1, IS-1, LV-1 and IS-4 standards, amongst other standards.

In some embodiments, the cancer therapy stimulation lead 1400 can further include a fixation element 1412, such as an element that can adhere to a portion of the subject's body to maintain the position of the cancer therapy stimulation lead 1400 and/or the electrodes 1408. In various embodiments, the fixation element 1412 can be disposed along the distal end 1406 of the cancer therapy stimulation lead 1400. However, in some embodiments a fixation element 1412 is omitted.

Figure 15:
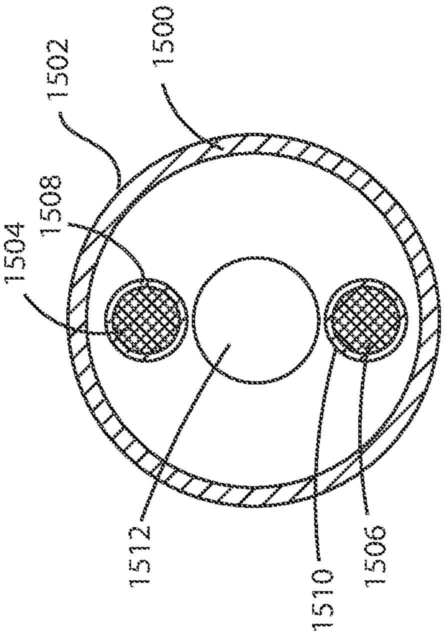
FIG. 15 is a cross-sectional schematic view of a cancer therapy stimulation lead in accordance with various embodiments herein.

Referring no to FIG. 15, a cross-sectional schematic view of a cancer therapy stimulation lead 1400 as taken along line 6-6' of FIG. 14 is shown in accordance with various embodiments herein. The cancer therapy stimulation lead 1400 can include an outer layer 1500 with an outer surface 1502. The outer layer 1500 can be flexible and can be configured to protect other components disposed within the lumen of the outer layer 1500. In some embodiments, the outer layer 1500 can be circular in cross-section. In some embodiments, the outer layer 1500 includes a dielectric material and/or an insulator. In some embodiments, the outer layer 1500 can include various biocompatible materials such as polysiloxanes, polyethylenes, polyamides, polyurethane and the like.

In various embodiments, the cancer therapy stimulation lead 1400 can include one or more conductors, such as a first conductor 1504 and a second conductor 1506. In some embodiments, the first conductor 1504 and the second conductor 1506 can be disposed within the lumen of the outer layer 1500. The first conductor 1504 and a second conductor 1506 can be configured to provide electrical communication between an electrode 1408 and the proximal end 1404 of the cancer therapy stimulation lead 1400. The first conductor 1504 and a second conductor 1506 can include various materials including copper, aluminum, silver, gold, and various alloys such as tantalum/platinum, MP35N and the like. An insulator 1508 and 1510 can surround the first conductor 1504 and a second conductor 1506. The insulators 1508 and 1510 can include various materials such as electrically insulating polymers.

In some embodiments, each of the electrodes 1408 can have individual first conductors 1504 and second conductors 1506 to electrically couple the electrode 1408 to the proximal end 1404 of the cancer therapy stimulation lead 1400. However, in some embodiments, each of the electrodes 1408 only connects to a single conductor to electrically couple the electrode 1408 to the proximal end 1404 of the cancer therapy stimulation lead 1400. In some embodiments, the first conductor 1504 and a second conductor 1506 can be configured as a coil or a cable. Multiple conductors can be disposed within the lumen of the outer layer 1500. For example, a separate conductor or set of conductors can be in communication with each electrode disposed along the lead.

In various embodiments, a first conductor 1504 and a second conductor 1506 can form a part of an electrical circuit by which the electric fields from the electric field generating circuit are delivered to the site of the cancerous tissue. Many more conductors than are shown in FIG. 15 can be included within embodiments herein. For example, the cancer therapy stimulation lead 1400 can include 1, 2, 3, 4, 5, 6, 7, 8, 10, 15 or 20 or more conductors, or any number of conductors falling within a range between any of the foregoing.

In some embodiments, the cancer therapy stimulation lead 1400 can include a central channel 1512. The central channel 1512 can be configured for a guide wire, or other implanting device, to pass through, such as to aid in implanting the cancer therapy stimulation lead 1400 and electrodes 1408. In some cases, additional channels (not shown) are disposed within the cancer therapy stimulation lead 1400.

Medical Visualization System Features

In an embodiment, a medical visualization system is included. The medical visualization system can include a video processing circuit, and a central processing circuit in communication with the video processing circuit, and a communications circuit in communication with the central processing circuit. The medical visualization system can also include a user interface generated by the video processing circuit. The user interface can include a three-dimensional model of at least a portion of a subject's anatomy from a first perspective. The first perspective can be configured to be controlled by a user.

The medical visualization system herein can be configured to display a variety of information to a user. In some embodiments, the medical visualization system can be configured to present information on the user interface that notifies a user of an electric field strength. In some embodiments, the medical visualization system can be configured to present information on the user interface that notifies a user of placing one or more additional cancer therapy stimulation leads to increase a field strength, optimize the field strength covering a targeted area for therapy, optimize field strength in view of acceptable levels of heating, etc.

In some embodiments, the medical visualization system can be configured to present information on the user interface that notifies a user when the at least one cancer therapy stimulation lead is placed within a threshold value or distance of a critical structure. Such threshold values or distances can be set by the system user and/or can be preset within the system. In some embodiments, the medical visualization system can be configured to present information on the user interface that notifies a user of critical structures (such as critical anatomical structures) comprising at least one selected from the group including of bone, pituitary gland, blood vessels, hypothalamus, brain ventricles, brain stem, amygdala, thalamus, cerebellum, and corpus callosum, or other structures that may be designated by the user or preset within the system.

In various embodiments, the medical visualization system can be configured to present regions of interest to the user that can include surgical entry sites, lead implantation sites, such as for example the suggested placement of a burr hole or multiple burr holes for inserting one or multiple cancer therapy stimulation leads. In some embodiments, the medical visualization system can be configured to present information on the user interface that includes a graphic representation of a burr hole placement within a subject's skull. In various embodiments, the graphic representation of the burr hole provides a graphic representation of optimal burr hole placement. In an embodiment, the visual burr hole representation is shown to be at least 0.25 inch in diameter. In an embodiment, the visual burr hole representation is shown to be approximately 0.625 inches in diameter.

In some embodiments, the medical visualization system can be configured to present information on the user interface that includes a visual lead trajectory, where the visual lead trajectory provides a graphic representation of an optimal trajectory of the at least one cancer therapy stimulation lead.

In some embodiments, the medical visualization system can be configured to present information on the user interface that includes a visual thermal representation of the at least a portion of a subject's anatomy, where the visual thermal representation of the at least a portion of a subject's anatomy is associated with the three-dimensional model. In some embodiments, the medical visualization system is configured to present information to a user that shows where the visual thermal representation of the at least a portion of a subject's anatomy estimates temperatures throughout the three-dimensional model (which can be a portion of a particular anatomical structure or body part or can be the entirety of the anatomical structure or body part—such as the entire head or the entire brain, etc.).

In some embodiments, the medical visualization system can be configured to display an electrode position to provide a therapy based on a location of the cancerous tumor or tumor resection site. In some embodiments, the medical visualization system is configured to present information to a user that displays placement of one or more cancer therapy stimulation leads based on a location the cancerous tumor or tumor resection site. In some embodiments, the medical visualization system is configured to present information to a user that displays placement of one or more electrodes based on a location of the cancerous tumor or tumor resection site.

Beyond cancerous tumors and tumor resection sites, it will be appreciated that systems herein can also be used to visualize aspects of electrical field therapy with respect to contrast enhanced volumes/regions/zones.

In some embodiments, the medical visualization system is configured to present information to a user that displays a predetermined therapy parameter comprising a duty cycle based on a location of the cancerous tumor or tumor resection site. In some embodiments, the medical visualization system is configured to present information to a user that displays one or more therapy vector patterns between electrodes.

In some embodiments, the medical visualization system includes a device including a graphical display and a machine-readable medium comprising instructions. The instructions can perform various operations when implemented by one or more processors. By way of example, the operations can include those in accordance with methods or operations as described herein. The machine-readable medium can include random access memory (RAM), read-only memory (ROM), magnetic data storage media, optical data storage media, flash memory, and the like.

Figure 16:
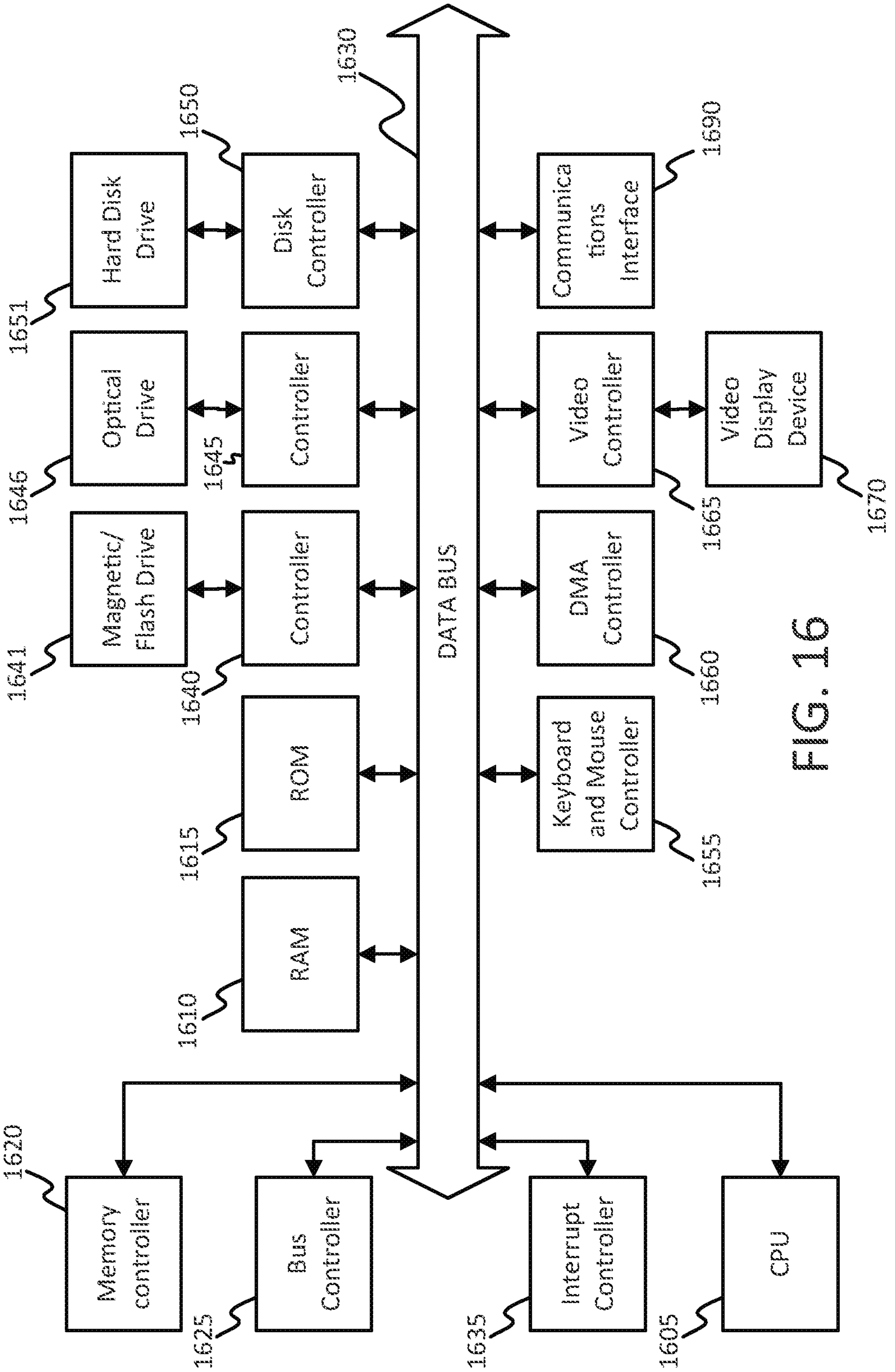
FIG. 16 is a diagram of various components of a medical visualization system in accordance with various embodiments herein.

Devices to display three-dimensional models of at least a portion of a subject's anatomy and/or user interface for the same can include various components. Referring now to FIG. 16, a diagram of various components is shown in accordance with some embodiments. The medical visualization system can include a central processing circuit that can include various components such as a central processing unit. By way of example, the medical visualization system can include a central processing unit (CPU) 1605 or processor, which may include a conventional microprocessor, random access memory (RAM) 1610 for temporary storage of information, and read only memory (ROM) 1615 for permanent storage of information. A memory controller 1620 is provided for controlling system RAM 1610. A bus controller 1625 is provided for controlling data bus 1630, and an interrupt controller 1635 is used for receiving and processing various interrupt signals from the other system components.

Mass storage can be provided by a magnetic or flash memory drive 1641 including removable or non-removable media, which is connected to bus 1630 by controller 1640, an optical drive such as CD-ROM or DVD drive 1646, which is connected to bus 1630 by controller 1645, and/or hard disk drive 1651 (magnetic or solid state), which is connected to bus 1630 by controller 1650. In some embodiments, mass storage can be provided by a device connected through a universal serial bus (USB), eSATA, FireWire, or Thunderbolt interface or other type of connection. User input to the programmer system may be provided by a number of devices. For example, a keyboard and mouse can be connected to bus 81630 by keyboard and mouse controller 1655. DMA controller 1660 is provided for performing direct memory access to system RAM 1610. In some embodiments user input can be provided by a pen, light pen, glove, wearable object, gesture control interface, or the like.

A video processing circuit can be included and can generate a user interface. The video processing circuit can include a video controller 1665 or video output, which controls video display 1670. In some embodiments, the video controller 1665 can also include one or more graphical processing units (GPUs). The video processing circuit can be in communication with the central processing circuit.

The medical visualization system can also include a communications interface 1690 or communications circuit which allows the system to interface and exchange data with other systems and/or servers. The communications circuit can be in communication with the central processing circuit. In some embodiments, the communications interface 1690 can include a network interface card or circuit to facilitate communication with a packet switched (such as IP) or other type of data network.

It will be appreciated that some embodiments may lack various elements illustrated in FIG. 16. In addition, the architecture shown in FIG. 16 is merely one example of how discrete components can be arranged and other architectures are explicitly contemplated herein.

In addition to, or instead of, the components described with respect to FIG. 16, it will be appreciated that the system can also include a microcontroller, a programmable logic controller (PLC), an ASIC, an FPGA, a microprocessor, or other suitable technology.

The video processing circuit (either locally or on a remote node) can generate a 3D (or fewer or more dimensions) image based on information including one or more of geometry, viewpoint, texture, lighting and shading information, and other information described above. In some embodiments, information for rendering an image is combined within a scene file. The term "graphics pipeline" can be used to refer to the sequence of steps used to create a 2D raster representation of a 3D scene. The video processing circuit can execute one or more steps of the graphics pipeline. The video processing circuit can also include one or more physical components used in the graphics pipeline. Using the information described above, the graphics pipeline can include one or more stages of creating a scene out of geometric primitives, modelling and transformation, camera transformation, lighting, projection transformation, clipping, scan conversion or rasterization, and texturing and fragment shading. In various embodiments, other operations can also be performed. In various embodiments, the graphics pipeline can use OpenGL, DirectX, or other protocols.

Methods

Many different methods are contemplated herein, including, but not limited to, methods of making, methods of using, and the like. Aspects of system/device operation described elsewhere herein can be performed as operations of one or more methods in accordance with various embodiments herein.

Figure 17:
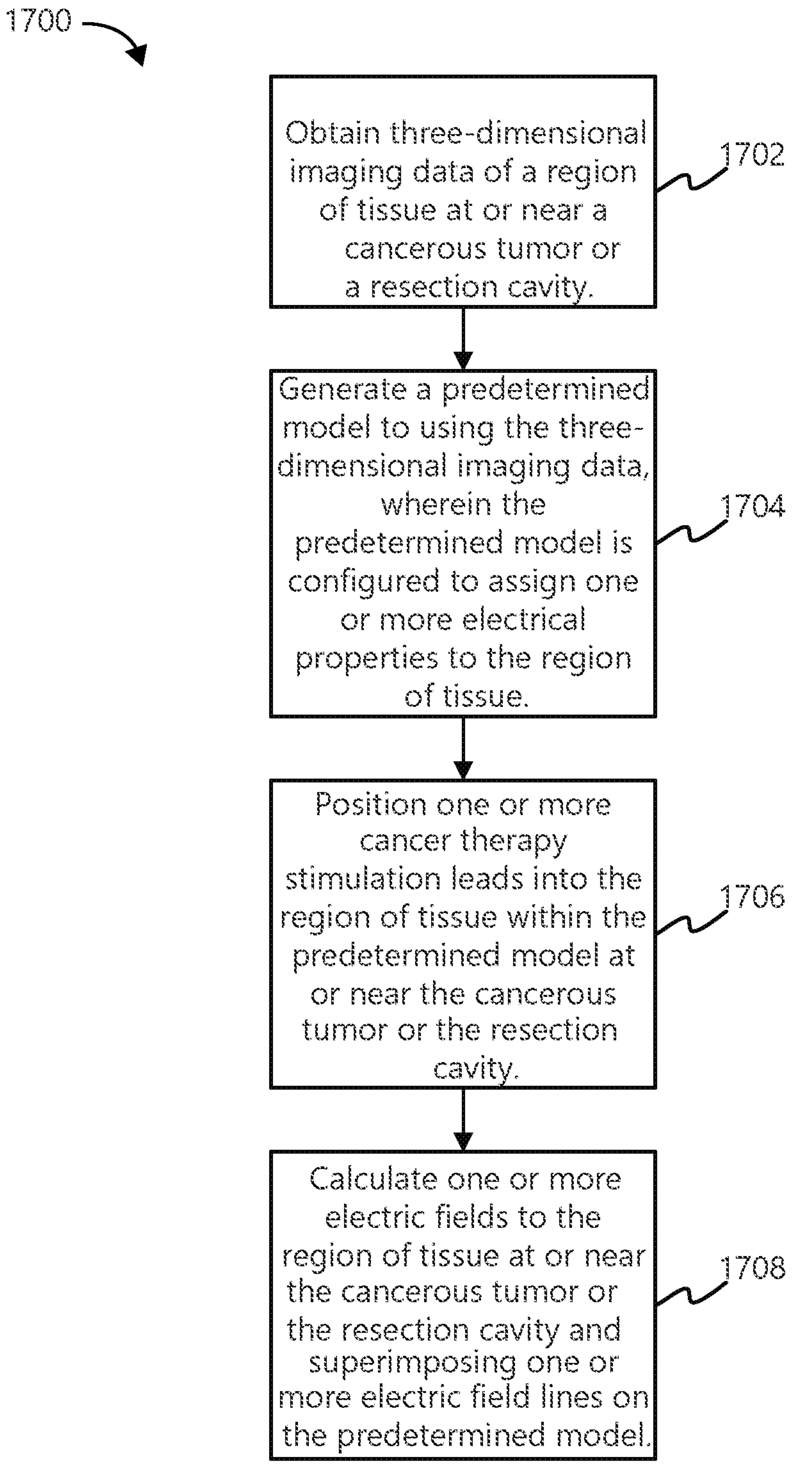
FIG. 17 is a method for visualizing placement of a cancer therapy stimulation lead in accordance with various embodiments herein.

Referring now to FIG. 17, in an embodiment, a method 1700 for visualizing cancer treatment lead placement is included. The method can include obtaining three-dimensional imaging data of a region of tissue at or near a cancerous tumor or a tumor resection cavity at 1702. The method can further include generating a predetermined model using the three-dimensional data at 1704. The predetermined model being configured to assign one or more electrical properties to the region of tissue. The method further including positioning one or more cancer therapy stimulation leads into the region of tissue within the predetermined model at or near the cancerous tumor or the tumor resection cavity at 1706. The method further including calculating one or more electric fields to the region of tissue at or near the cancerous tumor or the tumor resection cavity and superimposing one or more electric field lines on the predetermined model at 1708.

In an embodiment, the method can further include calculating one or more temperatures of the region of tissue at or near the cancerous tumor or the tumor resection cavity and superimposing one or more temperature contours onto the predetermined model.

In an embodiment, the predetermined model being configured to predict changes to the region of tissue over a period of time.

In an embodiment, the changes result from a void or tissue swelling left behind by a resection of the cancerous tumor.

In an embodiment, the one or more electrical properties are assigned based on the type of tissue.

In an embodiment, the type of tissue including at least one selected from the group including of cancerous tissue, muscle, bone, and healthy tissue.

In an embodiment, the method further including setting a maximum temperature limit for healthy tissue.

In an embodiment, the method further including setting a maximum temperature limit for cancerous tissue.

In an embodiment, the method further including setting a minimum electric field strength.

In an embodiment, the one or more cancer therapy stimulation leads are independently controlled.

In an embodiment, the one or more cancer therapy stimulation leads include one or more electrodes.

In an embodiment, the one or more cancer therapy stimulation leads can include a component that can be used to measure temperature. For example, in some embodiments cancer therapy stimulation leads can include a thermistor, a thermocouple, a resistance temperature detector, a semiconductor junction-based temperature measuring component, or the like.

In an embodiment, the one or more cancer therapy stimulation leads includes a heat gradient and a therapy gradient that extend outward from the one or more cancer therapy stimulation leads.

In an embodiment, the three-dimensional imaging data is obtained using magnetic resonance imaging data or computerized tomography data.

Notifications

In an embodiment, the medical visualization system can include a notification system that presents one or more notifications to a user at the user interface. The notification system can notify a user about various things. For example, the notification system can warn a user when a cancer therapy stimulation lead is in proximity to one or more critical structures such as bone, nerves, pituitary gland, blood vessels, hypothalamus, brain ventricles, brain stem, amygdala, thalamus, cerebellum, or corpus callosum.

Additionally, the notification system can warn a user when an electric field strength zone generated by a cancer therapy stimulation lead decreases and/or increases in electric field strength based on a preset strength or when the electric field strength falls within a threshold value. Similarly, the notification system can warn a user when a cancer therapy stimulation lead or surrounding tissue decreases and/or increases in temperature based on a preset temperature or when the temperature crosses or falls within a threshold value.

The notification system can indicate to a user when it may be desirable to place one or more additional cancer therapy stimulation leads or one or more additional electrodes to increase the electric fields strength. The one or more additional electrodes could be selected from the group consisting of subcutaneous electrodes, sub-cranial electrodes, and external electrodes.

The notification system can notify a user about any of the above using a variety of means. For example, the notification system could provide a pop-up alert on the user interface. The notification system could provide a sound alert. The notification system could provide a textural and/or color change in the graphic representation of the user interface of the cancer therapy stimulation leads, subject's anatomy, critical structures, and/or cancerous tumor.

Tumor Resection Cavity

Figure 18:
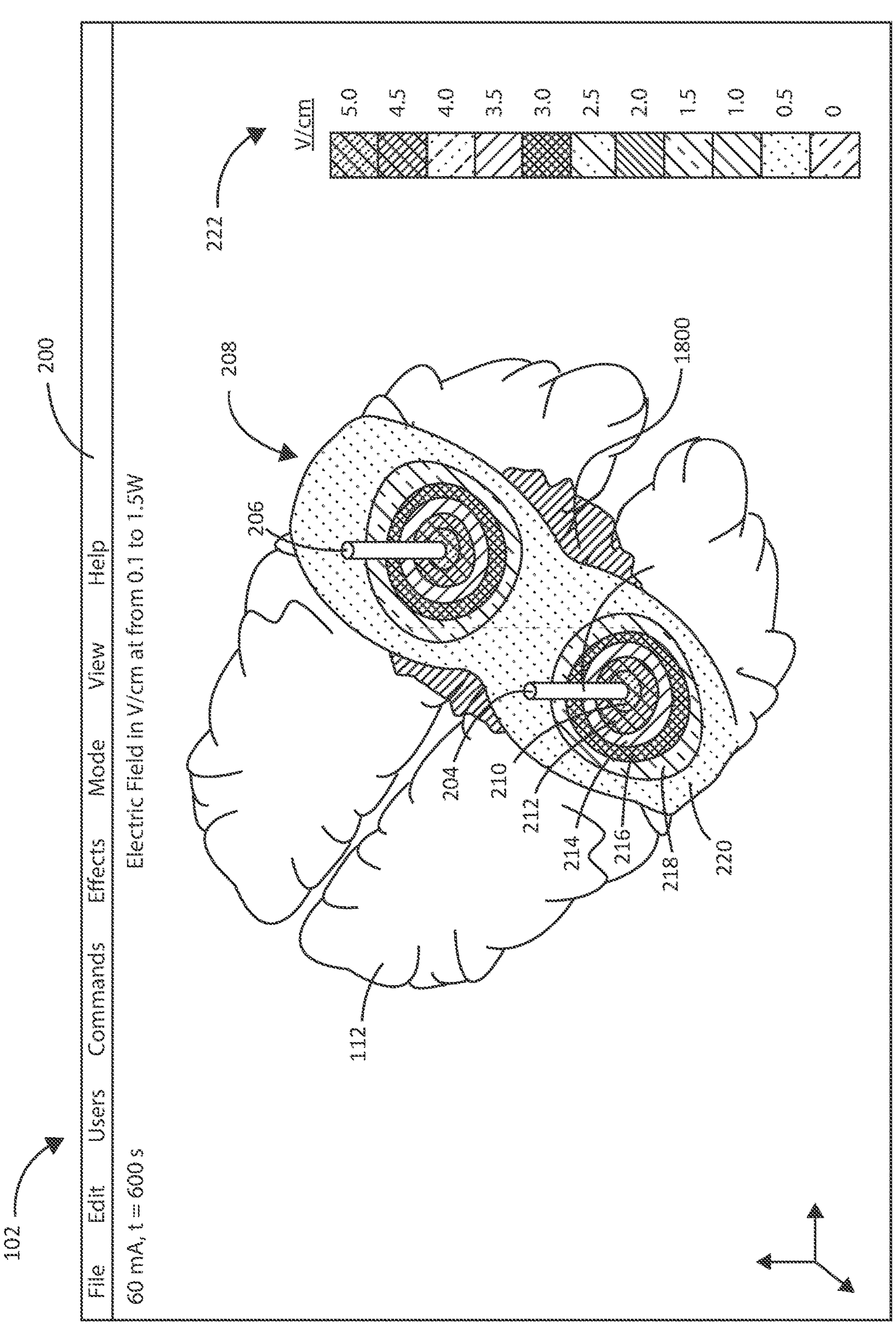
FIG. 18 is a schematic view of a user interface illustrating an electric field strength zone in accordance with various embodiments herein.

As previously discussed herein, the medical visualization system can be configured to provide optimal placement of one or more cancer therapy stimulation leads and can provide a graphic representation of an electric field zone overlaid at the site of lead placement on the three-dimensional model. The area treated may be a cancerous or non-cancerous tumor, a tumor resection site, zone, or cavity (such as to prevent recurrence of a cancer), pre-cancerous lesions, zones, contrast-enhanced tissue such as that proximal to a resection or tumor, or other tissues areas of concern or at risk, or other cancers or related or non-related conditions. Referring now to FIG. 18, a graphic representation of electric field strength zone 208 as associated with cancer therapy stimulation leads 204 and 206 positioned at a treatment site. The treatment site can include an area 1800 inclusive of a tumor resection cavity or other tissue targeted for treatment. The user interface 102 can display a graphic representation of at least one cancer therapy stimulation lead positioned within the three-dimensional model of the subject's anatomy at a treatment site. In the embodiment shown in FIG. 18, two cancer therapy stimulation leads 204 and 206 are present on opposing sides of the area 1800. In some embodiments, the cancer therapy stimulation leads 204, 206 can be positioned within the area 1800. In other embodiments, the cancer therapy stimulation leads 204, 206 can be positioned around the area 1800 within the treatment site. While FIG. 18 shows two cancer therapy stimulation leads, it will be appreciated that in some embodiments, the user interface 102 can display from 1 to 5 cancer therapy stimulation leads. In various embodiments, the user interface 102 can display 1, 2, 3, 4, or 5 cancer therapy stimulation leads. In various embodiments, more than 5 cancer therapy stimulation leads can be used.

The graphic representation of the electric field strength zone 208 can include one or more gradients of electric field strengths as represented by electric field strengths 210, 212, 214, 216, 218, and 220 that decrease in intensity in a radial direction away from the center of the cancer therapy stimulation lead 204. It will be appreciated each cancer therapy stimulation therapy lead in the graphic representation can include an electric field strength gradient. In various embodiments, each cancer therapy stimulation therapy lead can include the same electric field strength gradient. In various other embodiments, each cancer therapy stimulation therapy lead can include a different electric field strength gradient.

An electric field strength scale 222 including values for electric field strengths can be included in the user interface 102 as a legend to identify a value for the electric field strengths depicted on the display. While the electric field strengths in FIG. 18 are represented as discrete regions within the electric field strength zone 208, it will be appreciated that electric field strength can decrease in strength in a radial direction away from the center of the cancer therapy stimulation leads in a diffuse gradient (or continuous gradient) rather than in discrete circular regions (or stepped gradient).

In various embodiments, the electric field strengths modeled by the medical visualization system can be calculated using a variety of methods and include a variety of electric field strengths as previously described herein.

In some embodiments, the system can be configured to accept user input regarding a zone of interest around the resection cavity site. For example, the user input can mark a resection cavity site (or that information can be pre-inserted) and specify a particular distance (such as 0.5, 1, 2, 3, 4, 5, 6, 7, 8, 9, or 10 cm or more, or a number falling within a range between any of the foregoing) and then the calculated field strengths within that zone are displayed by the medical visualization system. In that manner, the system can specifically highlight information regarding field strengths in an area of most interest to the clinician or other system user. In some embodiments, the system can be configured to show gradients of field strength within the zone of interest. In some embodiments, the system can be configured to show areas within the zone of interest where the field strength crosses a threshold value (such as exceeding a minimum threshold value) as set through user input.

Figure 19:
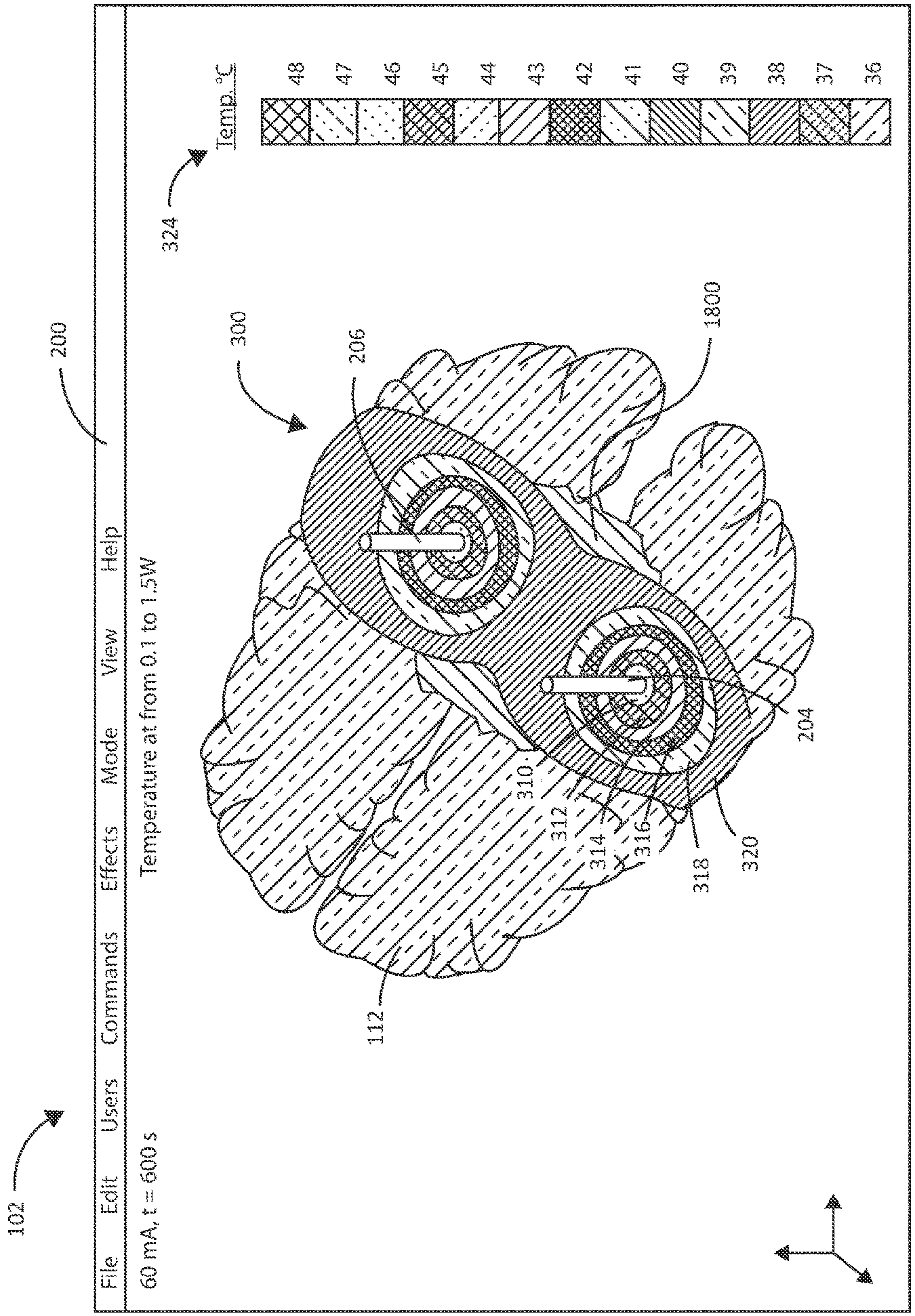
FIG. 19 is a schematic view of a user interface illustrating thermal heating zone in accordance with various embodiments herein.

Additionally, as previously discussed herein, the medical visualization system herein can also be configured to model a thermal heating zone associated with cancer therapy stimulation leads, which can also be used to further refine placement of the cancer therapy stimulation leads. In various embodiments, the average heat delivered will be generally proportional to electrode power multiplied by the duty factor. Referring now to FIG. 19, a schematic view of a user interface 102 illustrating an embodiment of a graphic representation of a thermal heating zone is shown in accordance with various embodiments herein. The user interface 102 can include a three-dimensional model of at least a portion of a subject's anatomy, such as the brain 112. The three-dimensional model of the subject's anatomy can also include an area 1800 that can include a tumor resection site or cavity.

The user interface 102 can display a graphic representation of at least one cancer therapy stimulation lead positioned within the three-dimensional model of the subject's anatomy at a treatment site. In the embodiment shown in FIG. 19, two cancer therapy stimulation leads 204 and 206 are present on opposing sides of the treatment area 1800. While FIG. 19 shows two cancer therapy stimulation leads, it will be appreciated that in some embodiments, the user interface 102 can display from 1 to 5 cancer therapy stimulation leads. In various embodiments, the user interface 102 can display 1, 2, 3, 4, or 5 cancer therapy stimulation leads. In various embodiments, more than 5 cancer therapy stimulation leads can be used.

The medical visualization system herein can be configured to provide optimal placement of one or more cancer therapy stimulation leads and can provide a graphic representation of a thermal heating zone overlaid at the site of lead placement on the three-dimensional model. FIG. 19 includes a virtual thermal heating zone 300 as associated with cancer therapy stimulation leads 204 and 206. The graphic representation of the thermal heating zone 300 can include one or more gradients of thermal heating that including temperatures 310, 312, 314, 316, 318, and 320 that can decrease in intensity in a radial direction away from the center of the cancer therapy stimulation lead 204. It will be appreciated each cancer therapy stimulation therapy lead in the graphic representation can include a thermal heating zone gradient. In various embodiments, each cancer therapy stimulation therapy lead can include the same thermal heating zone gradient. In various other embodiments, each cancer therapy stimulation therapy lead can include a different thermal heating zone gradient.

A temperature scale 324 can be included in the user interface 102 as a legend to identify a value for the temperatures depicted on the display. While the temperatures in FIG. 19 are represented as discrete regions within the thermal heating zone 300, it will be appreciated that temperature will decrease in strength in a radial direction away from the center of the cancer therapy stimulation leads in a diffuse gradient (or continuous gradient) rather than distinct circular regions (or stepped gradient).

The user interface 102 can display the thermal heating zone around the cancer therapy stimulation leads extending in a radial direction away from a center point of the cancer therapy stimulation leads. In some embodiments, the temperature of the thermal heating zone can be between 36° C. and 48° C. In some embodiments, the temperature can be greater than or equal to 36° C., 37° C., 38° C., 39° C., 40° C., 41° C., 42° C., 43° C., 44° C., ° C., 46° C., 47° C., or 48° C., or can be an amount falling within a range between any of the foregoing.

In various embodiments, the thermal heating zone modeled by the medical visualization system can be approximated using a variety of methods as previously discussed herein. The thermal heating zone can be modeled at a variety of delivery powers as previously discussed herein.

In some embodiments, the medical visualization system can be configured to allow a user to manipulate a position of one or more cancer therapy stimulation leads and the medical visualization system 100 can recalculate the position and values for the electric field strength zone 208 and the thermal heating zone 300. The user interface 102 can be updated during such a recalculation to display new position data for the cancer therapy stimulation lead(s) as manipulated by the user. The user interface 102 can also be updated during such a recalculation to display new and an updated electrical field strength and/or thermal heating zone information.

It will be appreciated that heating effects are sensitive to the duty factor of the therapy. As such, in various embodiments herein the system can model the impact of duty factor on heating. For example, the system can receive input from the user regarding a particular duty factor value and then apply the same in calculations herein (heating, field strength, etc.) to show the impact of the duty factor setting to the user.

In some embodiments, the medical visualization system can be configured to allow a user to mark a point of interest and see the temperature of the thermal heating zone at that point. For example, the system can be configured to allow the user to select a specific point or structure (using, for example, a mouse, a pen input device, a touch screen or the like) and see (such as through a pop-up box or a text field or graphic object) the temperature associated with that particular point of interest or structure.

It will be appreciated, that the medical visualization system can be configured to display both the thermal heating zone and the electric field strength associated with cancer therapy stimulation leads. By having the medical visualization system present both the thermal heating zone and the electric field strengths simultaneously, the user can refine the placement of the stimulation leads for optimal placement using the modeling data associated with the thermal heating zone and the electric field strength. Additionally, the user can visual how refining the placement of the stimulation leads affects both the thermal heating zone and the electric field strengths. Additionally, the user can refine settings applied for the therapy such as duty factor settings, active electrodes, therapy stimulation vectors, vector switching patterns, power, and the like.

System Recommendations

The medical visualization system embodied herein can be configured to recommend one or more optimized parameters to a user. The medical visualization system can be configured to calculate the optimized parameters using one or more optimization functions or algorithms. The optimization functions can include consideration of factors such as the average field strength of the treatment site, the calculated electric field strengths at varying positions within the treatment area, the average temperature across the treatment area, the calculated thermal heating zone across the treatment area, the tissue density and type within and around the treatment site, the location and types of critical structures within and around the treatment site, and the location of the cancerous tumor or the resection cavity to be treated.

Optimization functions or algorithms used herein can include differentiable and non-differentiable objective functions (e.g., those that use derivatives and those that do not). Optimization functions or algorithms herein can include, but are not limited to first-order derivative approaches, gradient approaches, partial derivative approaches, second-order derivative approaches, Hessian matrix based approaches, bracketing algorithms (such as Fibonacci search, golden section search, bisection method), local descent algorithms, gradient descent algorithms, Newton's method, secant method, quasi-Newton methods, direct algorithms (including cyclic coordinate search, Powell's method, Hooke-Jeeves method, Nelder-Mead simplex search), stochastic algorithms (including simulated annealing, evolution strategy, cross-entropy method), and population algorithms (including genetic algorithms, differential evolution methods, particle swarm optimization, and the like).

In some embodiments, the medical visualization system can provide recommendations to the user based on one or more optimization functions. In some embodiments, the medical visualization system calculates the optimal parameters to ensure the subject's anatomy can be treated safely and effectively.

For example, the medical visualization system can recommend the optimal number of cancer therapy stimulation leads and/or electrodes to use to treat a cancerous tumor or resection cavity. In some embodiments, the medical visualization system can display, on the user interface, the optimal number of cancer therapy stimulation leads and/or electrodes to use. In other embodiments, the medical visualization system can notify the user of the of the optimal number of cancer therapy stimulation leads and/or electrodes to use using one or more of the notification means described previously herein. In some examples, the optimal number of cancer therapy stimulation leads and/or electrodes can be a number sufficient to increase a field strength to at least a threshold value over a targeted area for therapy, a number of sufficient to generate a field strength crossing a threshold value over a targeted area for therapy in view of acceptable levels of heating, etc. For example, in some embodiments, the system can execute an optimization function (such as those described herein) to determine whether the use of a particular number of leads (e.g., 2 vs. 3 vs. 4, etc.) offers a benefit in terms of the field strength achieved (average or another measure) over a targeted area for therapy (such as a tumor resection site, a tumor, or the like) in view of heating effects. If, for example, the system determines that the use of 3 leads offer a benefit (such as better average field strength over a targeted area or another benefit) then the system can provide such a recommendation to the user, such as through an indication on the user interface. The targeted area for therapy can be designated by the user by interfacing through the user interface and/or can be loaded in from another device or system, or can be preset.

Similarly, in some embodiments, the system can execute an optimization function (such as those described herein) to determine whether the use of a particular number of electrodes on each lead (e.g., 1 vs. 2 vs. 3 vs. 4, etc.) offers a benefit in terms of the field strength achieved (average or another measure) over a targeted area for therapy (such as a tumor resection site, a tumor, or the like) in view of heating effects. If, for example, the system determines that the use of a certain number of electrodes offers a benefit (such as better average field strength over a targeted area or another benefit) then the system can provide such a recommendation to the user, such as through an indication on the user interface.

Beyond the number of leads and/or electrodes, using a similar optimization approach, systems herein can also make recommendations regarding the type of leads and/or electrodes being used. For example, the system can make recommendations regarding the use of one or more additional leads/electrodes in the form of subcutaneous leads/electrodes, sub-cranial leads/electrodes, and external leads/electrodes. For example, in some cases the use of subcutaneous electrodes can be recommended to boost field strength in a targeted area for therapy.

In some embodiments, the medical visualization system can recommend the optimal placement of the cancer therapy stimulation leads at the treatment site. In some embodiments, the medical visualization system can display the optimal placement of the cancer therapy stimulation leads on the user interface. As before, the system can execute an optimization function (such as those described herein) to determine whether a particular placement of leads offers a benefit, such as in terms of the field strength achieved (average or another measure) over a targeted area for therapy (such as a tumor resection site, a tumor, or the like) in view of heating effects. If, for example, the system determines that a particular placement of leads offers a benefit (such as better average field strength over a targeted area or another benefit) then the system can provide such a recommendation to the user, such as through an indication on the user interface.

Additionally, the medical visualization system can recommend the optimal placement of the implantable field generator (IFG) unit. For example, the medical visualization system can recommend a site within the subject's anatomy to safely implant the IFG unit. In some embodiments, the medical visualization system may recommend implanting the IFG unit within the subject's brain. In other embodiments, the medical visualization system may recommend implanting the IFG unit further away from the cancer therapy stimulation leads, such as implanting the IFG unit in the subject's neck, chest, arm, or leg. In some embodiments, the system can execute an optimization function (such as those described herein) to determine whether a particular placement of the IFG offers sufficient room within the particular anatomy of a patient or otherwise offers a benefit, such as in terms of the field strength achieved (average or another measure) over a targeted area for therapy (such as a tumor resection site, a tumor, or the like) in view of heating effects.

In some embodiments, the medical visualization system can recommend the duty factor cycle timing or pattern of the cancer therapy stimulation leads. In some embodiments, the medical visualization system can recommend the vector and vector pattern between two or more electrodes. In some embodiments the system can execute an optimization function (such as those described herein) to determine whether a particular duty factor cycle timing or pattern of the cancer therapy stimulation leads offers a benefit, such as in terms of the amount of exposure of tissue to therapy herein or the field strength achieved (average or another measure) over a targeted area for therapy (such as a tumor resection site, a tumor, or the like) in view of heating effects. If, for example, the system determines that a particular duty cycle timing or pattern of the cancer therapy stimulation leads offers a benefit (such as better average field strength over a targeted area, total amount of exposure of the targeted area to the therapy, or another benefit) then the system can provide such a recommendation to the user, such as through an indication on the user interface.

Cancer Therapy Stimulation Lead Trajectory

The medical visualization system embodied herein can be configured to provide a visual lead trajectory for each cancer therapy stimulation lead. The visual lead trajectory can provide a graphic representation of the optimal trajectory of the cancer therapy stimulation leads from the entry point to the final placement of the lead. The visual lead trajectory can consider, among other things, the location of the cancerous tumor or resection cavity being treated, any critical structures the cancer therapy stimulations leads may encounter during implantation, and the size and number of the cancer therapy stimulation leads.

In some embodiments, the medical visualization system can recommend the optimal cancer therapy stimulation lead trajectory. The medical visualization system can recommend the optimal cancer therapy stimulation lead trajectory using one or more of the optimization functions as described previously herein. For example, the system can model a series of different lead trajectories and then using an optimization function determine optimal lead trajectories in terms of average field strength over a targeted area for therapy in view of thermal effects as merely one example. It will be appreciated, however, that optimization may performed in view of endpoints other than average field strength.

In many examples herein, leads have been illustrated as being parallel to one another or substantially parallel. However, it will be appreciated that non-parallel lead placements are also expressly contemplated herein and that system modeling, operations, recommendations, outputs, and the like can all be performed in the context of non-parallel lead placements.

Burr Hole Placement

The medical visualization system can include a user interface having a visual burr hole representation. The visual burr hole representation can provide a graphic representation of the optimal burr hole placement or placements for one, two, or more burr holes in a subject's head prior to surgery if cancer therapy stimulation leads are being implanted into the subject's brain to reach a cancerous tumor or a resection cavity.

In an embodiment, the graphic representation of the burr hole can be at least 0.25 inch in diameter. In some embodiments, the graphic representation of the burr hole can be approximately 0.625 inch in diameter. Thus, the graphic representation of the burr hole could be approximately 0.25 inch in diameter, 0.333 inch in diameter, 0.5 inch in diameter, or 0.625 inch in diameter, or can be an amount falling within a range between any of the foregoing.

In some embodiments, the medical visualization system can recommend the optimal burr hole placement or placements. The medical visualization system can recommend the optimal burr hole placement using one or more of the optimization functions as described previously herein. For example, the system can model a series of different burr hole placements and then using an optimization function determine an optimal burr hole placement in terms of average field strength over a targeted area for therapy in view of thermal effects as merely one example. It will be appreciated, however, that optimization may performed in view of endpoints other than average field strength.

Projected MRI Heating

The medical visualization system can be configured to provide a projected heating zone observed at a treatment site during an MM. Heating can occur during MM procedures due to time varying radiofrequency and gradient fields from the scanner inducing electrical currents. Under continuous RF exposure and without heat dissipation, the local tissue temperature can rise linearly in time with the absorbed RF power per exposed mass, the specific absorption rate (SAR). Applying one or more models for the SAR, the medical visualization system can calculate and provide a graphic representation of the expected thermal heating throughout the treatment site during an MM. In some embodiments, the projected heating zone includes the thermal heating expected during an MM when the subject has one or more cancer therapy stimulation leads implanted at the treatment site. The medical visualization system can consider the position of the cancer therapy stimulation leads, the size and number of cancer therapy stimulation leads and electrodes implanted within and around the treatment site, and the types of tissue within and around the treatment site that could be affected.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure.

Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical visualization system comprising:
a video processing circuit;
a central processing circuit, wherein the central processing circuit is in communication with the video processing circuit; and
a user interface, wherein the user interface is generated by the video processing circuit, the user interface comprising:
a three-dimensional model, the three-dimensional model comprising at least a portion of a subject's anatomy;
a graphic representation, the graphic representation comprising at least one cancer therapy stimulation lead; and
a visual thermal heating zone, wherein the visual thermal heating zone is associated with the graphic representation of the at least one cancer therapy stimulation lead.

2. The medical visualization system of claim 1, wherein the visual thermal heating zone provides a graphic representation of temperatures around tissue adjacent to the at least one cancer therapy stimulation lead.

3. The medical visualization system of claim 1, the three-dimensional model further comprising a cancerous tumor, resection cavity, or contrast enhanced region.

4. The medical visualization system of claim 3, wherein the user interface displays placement of one or more electrodes based on a location of the cancerous tumor, resection cavity, or contrast enhanced region.

5. The medical visualization system of claim 1,
wherein the user interface is configured to depict an initial position of the at least one cancer therapy stimulation lead calculated to avoid the one or more critical anatomical structures.

6. The medical visualization system of claim 1, wherein the user interface notifies the user of placing one or more additional cancer therapy stimulation leads to increase a field strength.

7. The medical visualization system of claim 1,
wherein the user interface notifies the user when the at least one cancer therapy stimulation lead is near a critical structure; and
the critical structure comprising at least one selected from the group consisting of bone, pituitary gland, blood vessels, hypothalamus, brain ventricles, brain stem, amygdala, thalamus, cerebellum, and corpus callosum.

8. The medical visualization system of claim 1, wherein the user interface notifies the user when a calculated temperature of a critical structure or other designated area exceeds a programmable maximum temperature value.

9. The medical visualization system of claim 1, the user interface further comprising at least one visual burr hole representation, wherein the at least one visual burr hole representation provides a graphic representation of optimal burr hole placement.

10. The medical visualization system of claim 1, the user interface further comprising a visual lead trajectory, wherein the visual lead trajectory provides a graphic representation of an optimal trajectory of the at least one cancer therapy stimulation lead.

11. The medical visualization system of claim 1, the user interface further comprising a visual thermal representation of the at least a portion of a subject's anatomy;
wherein the visual thermal representation estimates temperatures throughout the three-dimensional model; and
wherein the visual thermal representation is associated with the three-dimensional model.

12. The medical visualization system of claim 1, wherein aspects of the visual thermal heating zone are calculated based on therapy vector patterns between electrodes, a power for the electrodes, and a duty factor for the electrodes.

13. A medical visualization system comprising:
a video processing circuit;
a central processing circuit, wherein the central processing circuit is in communication with the video processing circuit; and
a user interface, wherein the user interface is generated by a video processing circuit, the user interface comprising
a three-dimensional model, the three-dimensional model comprising at least a portion of a subject's anatomy;
a graphic representation, the graphic representation comprising at least one cancer therapy stimulation lead;
a visual thermal heating zone, wherein the visual thermal heating zone is associated with a graphic representation of at least one cancer therapy stimulation lead; and
a notification system, wherein the notification system is configured to provide one or more notifications to the user.

14. The medical visualization system of claim 13, wherein the notification system notifies the user when the at least one cancer therapy stimulation lead is near one or more critical structures.

15. The medical visualization system of claim 13, wherein the medical visualization system notifies the user when a calculated temperature of a critical structure or other designated area exceeds a programmable maximum temperature value.

16. The medical visualization system of claim 13, wherein the notification system notifies the user of placing one or more additional electrodes to increase a field strength.

17. The medical visualization system of claim 16, the one or more additional electrodes comprising at least one selected from the group consisting of subcutaneous electrode, subcranial electrode, and external electrode.

18. The medical visualization system of claim 13, the notification system comprising at least one selected from the group consisting of pop-up alert, sound alert, textural change in the graphic representation, and color change in the graphic representation.

19. A medical visualization system comprising:
a video processing circuit;
a central processing circuit, wherein the central processing circuit is in communication with the video processing circuit; and a user interface, wherein the user interface is generated by the video processing circuit, the user interface comprising
a three-dimensional model, the three-dimensional model comprising at least a portion of a subject's anatomy;
a graphic representation, the graphic representation comprising at least one cancer therapy stimulation lead; and
a visual electrical field strength zone, wherein the visual electrical field strength zone is associated with the graphic representation of the at least one cancer therapy stimulation lead.

20. The medical visualization system of claim 19, wherein the user interface notifies the user of placing one or more additional cancer therapy stimulation leads to increase a field strength.

* * * * *